US011720817B2

(12) United States Patent
Patel et al.

(10) Patent No.: US 11,720,817 B2
(45) Date of Patent: Aug. 8, 2023

(54) WAVEFORM ANNOTATOR

(71) Applicant: Medical Informatics Corp., Houston, TX (US)

(72) Inventors: Raajen Patel, Houston, TX (US); Alexander Csicsery-Ronay, Taos, NM (US); Vincent Gagne, Taos, NM (US)

(73) Assignee: Medical Informatics Corp., Houston, TX (US)

( * ) Notice: Subject to any disclaimer, the term of this patent is extended or adjusted under 35 U.S.C. 154(b) by 1034 days.

(21) Appl. No.: 16/459,297

(22) Filed: Jul. 1, 2019

(65) Prior Publication Data

US 2021/0004710 A1 Jan. 7, 2021

(51) Int. Cl.

| | |
|---|---|
| ***A61B 5/00*** | (2006.01) |
| ***G06N 20/00*** | (2019.01) |
| ***G16H 15/00*** | (2018.01) |
| ***G16H 50/20*** | (2018.01) |
| ***G16H 30/40*** | (2018.01) |
| ***G16H 10/60*** | (2018.01) |
| ***A61B 5/339*** | (2021.01) |
| ***A61B 5/349*** | (2021.01) |

(52) U.S. Cl.

CPC ............. *G06N 20/00* (2019.01); *A61B 5/339* (2021.01); *A61B 5/349* (2021.01); *A61B 5/7435* (2013.01); *G16H 10/60* (2018.01); *G16H 15/00* (2018.01); *G16H 30/40* (2018.01); *G16H 50/20* (2018.01)

(58) Field of Classification Search

CPC .................................................... G06F 3/0481

See application file for complete search history.

(56) References Cited

U.S. PATENT DOCUMENTS

| | | | |
|---|---|---|---|
| 5,819,007 | A | 10/1998 | Elghazzawi |
| 7,188,151 | B2 | 3/2007 | Kumar et al. |
| 7,490,085 | B2 | 2/2009 | Walker et al. |
| 8,221,330 | B2 | 7/2012 | Sarkela et al. |
| 8,924,235 | B2 | 12/2014 | Seely |
| 9,289,135 | B2 | 3/2016 | LeBoeuf et al. |
| 9,357,934 | B2 | 6/2016 | Watson et al. |
| 9,400,874 | B2 | 7/2016 | Powell et al. |
| 9,498,146 | B2 | 11/2016 | Harlev et al. |
| 9,524,569 | B2 | 12/2016 | Moore et al. |
| 9,554,719 | B2 | 1/2017 | Banet et al. |
| 9,569,593 | B2 | 2/2017 | Santos |
| 9,569,594 | B2 | 2/2017 | Santos |
| 9,681,818 | B2 | 6/2017 | Govari et al. |
| 9,785,753 | B2 | 10/2017 | Santos |
| 9,846,764 | B2 | 12/2017 | Dziubinski et al. |
| 9,943,233 | B2 | 4/2018 | Lavi et al. |
| 9,962,111 | B2 | 5/2018 | Balakrishnan et al. |

(Continued)

*Primary Examiner* — Di Xiao

(74) *Attorney, Agent, or Firm* — Schafer IP Law; Richard A. Schafer

(57) ABSTRACT

A waveform annotator system allows clinicians to annotate a physiological data waveform, providing initial annotations based on a model corresponding to a type of the physiological data. The initial annotations may be modified by the clinician as desired. The annotations are saved in an annotation database for later use by the clinician and for training the model using machine learning to improve the initial annotations based on the modifications made by the clinician. The trained model may be distributed to other waveform annotator systems.

20 Claims, 21 Drawing Sheets

(56) References Cited

U.S. PATENT DOCUMENTS

| | | | |
|---|---|---|---|
| 10,159,415 | B2 | 12/2018 | Gopalakrishnan et al. |
| 10,199,124 | B2 | 2/2019 | Santos |
| 10,219,704 | B2 | 3/2019 | Lavi et al. |
| 10,262,382 | B2 | 4/2019 | Moore et al. |
| 2004/0122705 | A1 | 6/2004 | Sabol et al. |
| 2004/0122787 | A1 | 6/2004 | Avinash et al. |
| 2004/0204635 | A1 | 10/2004 | Scharf et al. |
| 2009/0171227 | A1* | 7/2009 | Dziubinski .......... A61B 5/7264 600/516 |
| 2010/0034442 | A1* | 2/2010 | Minakuchi ............. G16H 15/00 382/128 |
| 2010/0235782 | A1 | 9/2010 | Powell et al. |
| 2011/0218406 | A1 | 9/2011 | Hussain |
| 2012/0278099 | A1 | 11/2012 | Kelly et al. |
| 2013/0245463 | A1 | 9/2013 | Stuebe et al. |
| 2013/0271469 | A1 | 10/2013 | Moore et al. |
| 2013/0271470 | A1 | 10/2013 | Moore et al. |
| 2013/0275151 | A1 | 10/2013 | Moore et al. |
| 2013/0275152 | A1 | 10/2013 | Moore et al. |
| 2014/0107509 | A1 | 4/2014 | Banet et al. |
| 2014/0107511 | A1 | 4/2014 | Banet et al. |
| 2014/0107513 | A1 | 4/2014 | Banet et al. |
| 2014/0176554 | A1* | 6/2014 | Cohen .................... G16H 30/40 345/428 |
| 2015/0018700 | A1 | 1/2015 | Dziubinski et al. |
| 2017/0156592 | A1* | 6/2017 | Fu .......................... A61B 5/363 |
| 2017/0357764 | A1 | 12/2017 | Fauss et al. |
| 2017/0357765 | A1 | 12/2017 | Fauss et al. |
| 2018/0032493 | A1* | 2/2018 | Raleigh ................ G06Q 10/101 |
| 2018/0184931 | A1 | 7/2018 | Chen et al. |
| 2018/0206753 | A1 | 7/2018 | Weinberg et al. |
| 2018/0235497 | A1 | 8/2018 | Chen et al. |
| 2018/0277243 | A1 | 9/2018 | Qing et al. |
| 2018/0286500 | A1 | 10/2018 | Guerra |
| 2018/0296113 | A1 | 10/2018 | Stewart et al. |
| 2019/0029553 | A1 | 1/2019 | Chen et al. |
| 2019/0059763 | A1 | 2/2019 | Shakur et al. |
| 2019/0223739 | A1* | 7/2019 | Rapin .................... A61B 5/349 |
| 2019/0294954 | A1* | 9/2019 | Han ....................... G06V 10/82 |
| 2019/0317715 | A1* | 10/2019 | Tezuka .................... G06F 18/00 |
| 2019/0374166 | A1* | 12/2019 | Charles .................. G16H 50/20 |
| 2020/0194108 | A1* | 6/2020 | Podilchuk .............. G06V 10/25 |
| 2021/0133553 | A1* | 5/2021 | Van Den Heuvel ......................... G06V 10/7788 |

* cited by examiner

WAVEFORM ANNOTATOR

TECHNICAL FIELD

The present invention relates to the field of healthcare, and in particular to a technique for annotating physiological data waveforms.

BACKGROUND ART

Physicians and other clinicians often review captured physiological data of patients in waveform format. Annotations of that waveform data can be useful to clinicians, but the ability to do so has been limited. Probably most commonly, clinicians print a portion of the waveform data and make handwritten notes on paper. Some electronic tools allow placing calipers or measurement points on an electronically displayed waveform and doing basic calculations such as a time difference between the two measurement points. However, most commonly, those measurement points are ephemeral and must be printed to paper for loading into an electronic medical records (EMR) system. In addition, the number of measurement points that can be annotated in an interface are typically very limited.

SUMMARY OF INVENTION

According to one aspect, a method of annotating physiological waveform data comprises analyzing a physiological data waveform corresponding to a first type of physiological data, based on a model corresponding to the first type of physiological data; generating a first annotation automatically corresponding to the physiological data waveform based on the model; sending the first annotation and the physiological data waveform to a user display device; receiving a modification to the first annotation; creating a second annotation based on the modification; saving the second annotation in an annotation database; and training the model using machine learning based on the second annotation and the physiological. data waveform, generating a trained model.

According to a second aspect, a non-transitory machine-readable medium, on which are stored instructions for a machine, wherein the instructions comprise instructions that when executed cause the machine to: analyze a physiological data waveform corresponding to a first type of physiological data, based on a model corresponding to the first type of physiological data; generate a first annotation automatically corresponding to the physiological data waveform based on the model; send the first annotation and the physiological data waveform to a user display device; receive a modification to the first annotation; create a second annotation based on the modification; save the second annotation in an annotation database; and train the model using machine learning based on the second annotation and the physiological. data waveform, generating a trained model.

According to a third aspect, a waveform annotator system comprises: a database of physiological data; a database of waveform annotation data; a processor, programmed to: analyze a physiological data waveform corresponding to a first type of physiological data, based on a model corresponding to the first type of physiological data; generate a first annotation automatically corresponding to the physiological data waveform based on the model; send the first annotation and the physiological data waveform to a user display device; receive a modification to the first annotation;

create a second annotation based on the modification; save the second annotation in an annotation database; and train the model using machine learning based on the second annotation and the physiological. data waveform, generating a trained model.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
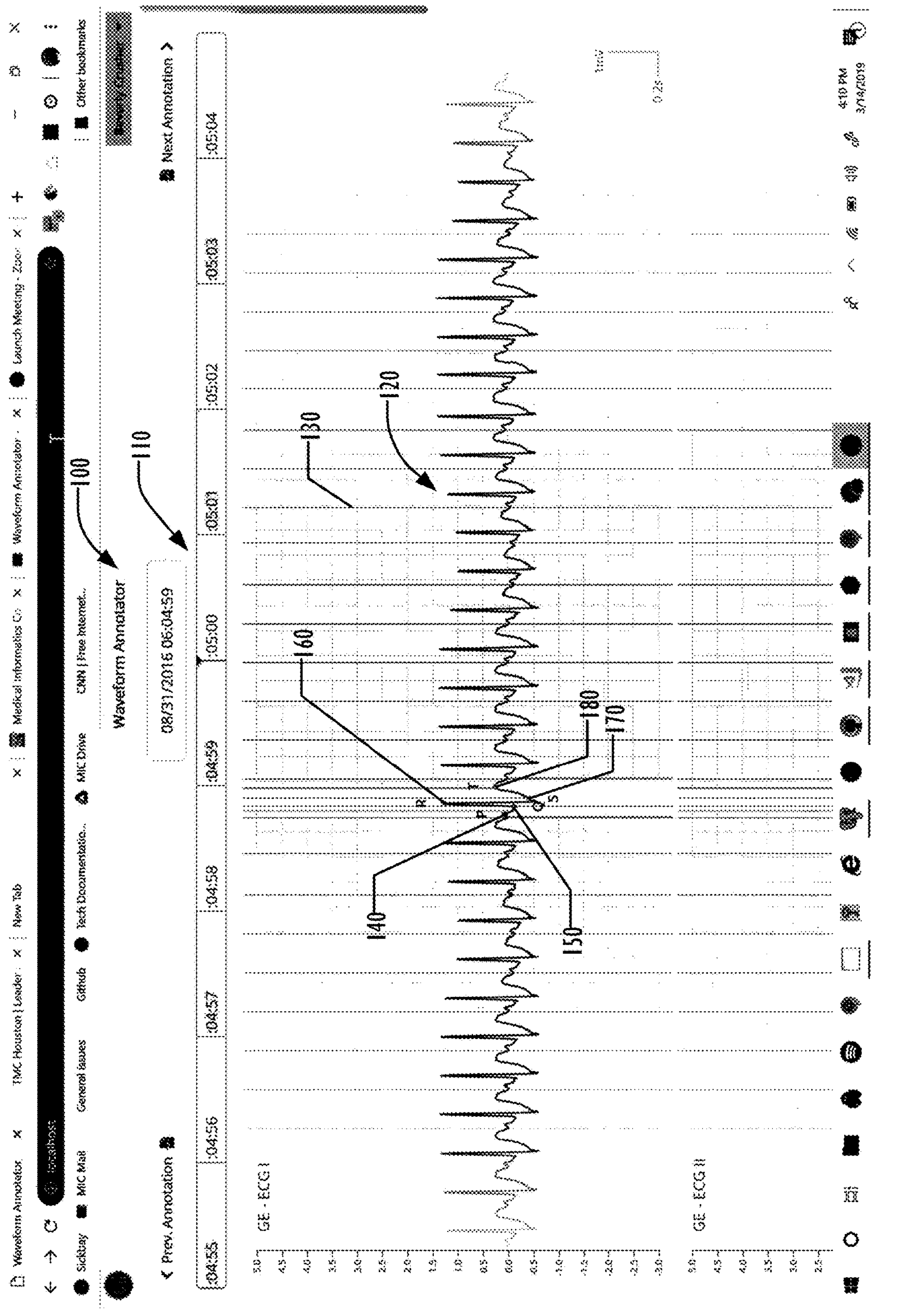
FIG. 1 is a screenshot illustrating an annotated physiological data waveform in a user interface of a waveform annotator according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment"

or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

The terms "a," "an," and "the" are not intended to refer to a singular entity unless explicitly so defined, but include the general class of which a specific example may be used for illustration. The use of the terms "a" or "an" may therefore mean any number that is at least one, including "one," "one or more," "at least one," and "one or more than one."

The term "or" means any of the alternatives and any combination of the alternatives, including all of the alternatives, unless the alternatives are explicitly indicated as mutually exclusive.

The phrase "at least one of" when combined with a list of items, means a single item from the list or any combination of items in the list. The phrase does not require all of the listed items unless explicitly so defined.

As used herein, the term "a computer system" can refer to a single computer or a plurality of computers working together to perform the function described as being performed on or by a computer system.

In this description, the term "couple" or "couples" means either an indirect or direct wired or wireless connection. Thus, if a first device couples to a second device, that connection may be through a direct connection or through an indirect connection via other devices and connections. The recitation "based on" means "based at least in part on." Therefore, if X is based on Y, X may be a function of Y and any number of other factors.

As used herein, the term "processing element" can refer to a single hardware processing element or a plurality of hardware processing elements that together may be programmed to perform the indicated actions. The hardware processing elements may be implemented as virtual hardware processing elements of a virtual programmable device hosted on a physical hardware device. Instructions that when executed program the processing element to perform an action may program any or all of the processing elements to perform the indicated action. Where the processing element is one or more multi-core processors, instructions that when executed program the processing element to perform an action may program any or all of the multiple cores to perform the indicated action.

As used herein, the term "medium" can refer to a single physical medium or a plurality of media that together store the information described as being stored on the medium.

As used herein, the term "memory" can refer to a single memory device or a plurality of memory devices that together store the information described as being stored on the medium. The memory may be any type of storage device, including random access memory, read-only memory, optical and electromechanical disk drives, etc.

In some embodiments, a waveform annotator system already knows what type of physiological data waveform is being displayed, and configures itself with annotation capabilities that are appropriate for the type of physiological data being displayed. In other embodiments, the waveform annotator system may be able to analyze the waveform and recognize the type of physiological data contained in the waveform, then select annotation capabilities based on that analysis.

In the discussion below, the waveform annotation system is generally illustrated as providing annotations on electrocardiogram (ECG) waveforms. However, ECG waveform annotations are illustrative and by way of example only, and embodiments can provide annotations on other types of physiological data waveforms. As used herein, the term "waveform" includes any type of physiological waveforms and vital sign time series data.

In one embodiment, illustrated in FIG. 1, the waveform annotator system can automatically detect heartbeats in the ECG waveform using on an ECG model that has been trained on large numbers of ECG waveforms. The waveform data may be obtained from a database of physiological data, then converted into a waveform. The waveform is displayed in the waveform annotator user interface. The layout and elements of the user interface illustrated in FIG. 1 are illustrative and by way of example only, and other layouts and user interface elements may be used as desired. As illustrated in FIG. 1, the user interface provides a waveform annotator area 100 that allows a user to select a patient and select a period of time for the display of the ECG waveform. The time period information is displayed in area 110. As illustrated in FIG. 1, a waveform 120 for one ECG lead is displayed, designated ECG I, but multiple ECG leads may be displayed, depending on scaling and display characteristics.

The ECG waveform 120 contains ECG physiological data that is collected or captured by sensors attached to the patient, processed by the underlying platform, and stored for analysis by clinicians. Clinicians may choose to look at real-time (current) physiological data or may select a period of time in the past for review.

Upon receiving input selecting a period of time for consideration, at least a portion of the physiological data waveform 120 for that period of time is displayed in the correct ECG ratio, preferably centered on a midpoint of the indicated time period. Depending on the time span of the selected period of time and the correct ECG ratio, the waveform for the entire period of time may not be displayable. The waveform annotator system then automatically detects the visible heartbeat intervals using the trained ECG model, denoting them with vertical lines 130. In some embodiments, a grid (omitted in FIG. 1 for clarity) may be displayed to allow the user to see finer time and amplitude information.

Because the system knows that waveform 120 is an ECG waveform, the trained ECG model allows the waveform annotator to make an initial annotation of key ECG elements that are placed in the display, such as the P, Q, R, S, and T features 140, 150, 160, 170, and 180. As is well known in the medical arts, one complete normal heartbeat includes a P-wave at the beginning, a QRS complex, and a T-wave at the end of the heartbeat. Abnormal heartbeats may vary and may omit one or more of the normal heartbeat features. Selecting one of the heartbeats causes the waveform annotator system to zoom into that heartbeat and present an annotation interface, such as is illustrated is illustrated in the user interface of FIG. 2. As is described in more detail in the discussion of FIG. 16 below, much of the computation for the waveform display and the associated annotations may be performed remotely to the display device.

The annotation interface provides a toolkit for making annotations. In an ECG annotation interface, the toolkit allows annotations indicating certain areas and certain peaks. Because the physiological data waveform is known to be an ECG signal, an ECG-signal specific algorithm is used to chop the waveform into heartbeats as marked by the vertical lines 130. In addition, P, Q, R, S, T points and segments are automatically placed on the waveform.

Figure 2:
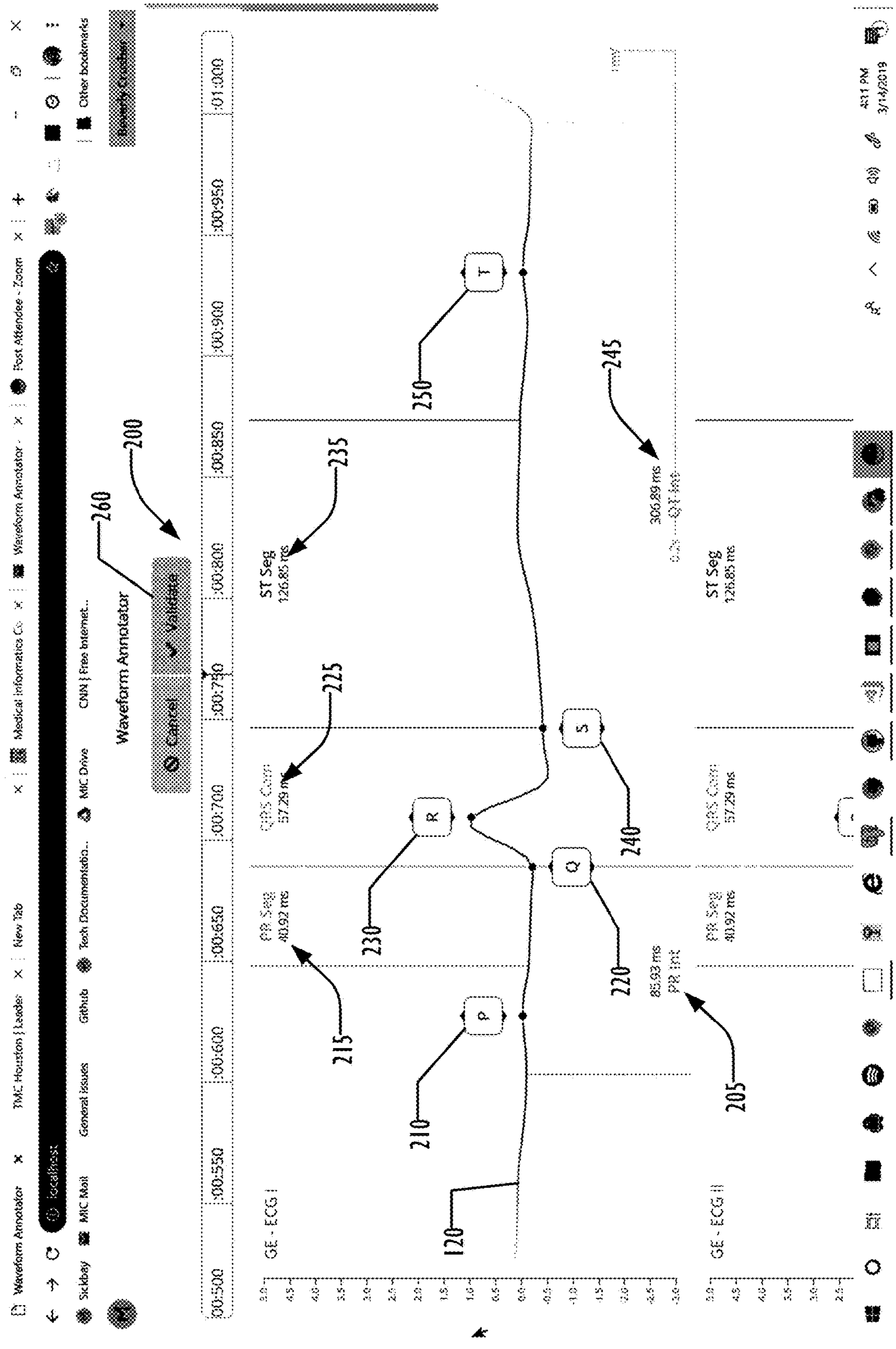
FIG. 2 is a screenshot illustrating a closeup view of an annotated physiological data waveform in the user interface of the waveform annotator according to one embodiment.

As illustrated in FIG. 2, the P, Q, R, S, and T points 210, 220, 230, 240, and 250, respectively are illustrated with a marker above or below the waveform 120 to denote those points on the waveform based on the algorithmic auto-detection. Segment features such as the PR interval 205, the PR segment 215, the QRS complex 225, the ST segment 235, and the QT interval 245 may also be identified and displayed, based on the P, Q, R, S, and T points 210, 220, 230, 240, and 250. Instead of a clinician manually attempting to measure or estimate the length of the PR interval 205, PR segment 215, QRS complex 225, ST segment 235, and QT interval 245, the user interface 200 may automatically provide exact measurements of those features in milliseconds as illustrated in FIG. 2. Although shown only for a single lead in FIG. 2, these features can be displayed on additional leads if the corresponding waveform is visible in the display, as can be seen in FIG. 2, where a portion of a second ECG lead (ECG II) is visible, showing markers delineating the PR segment 215, QRS complex 225, and ST segment 235 in that lead, too. The form of the markers 210, 220, 230, 240, and 250 for the P. Q. R., S, and T points is illustrative and by way of example only, and other forms of markers can be used.

Figure 3:
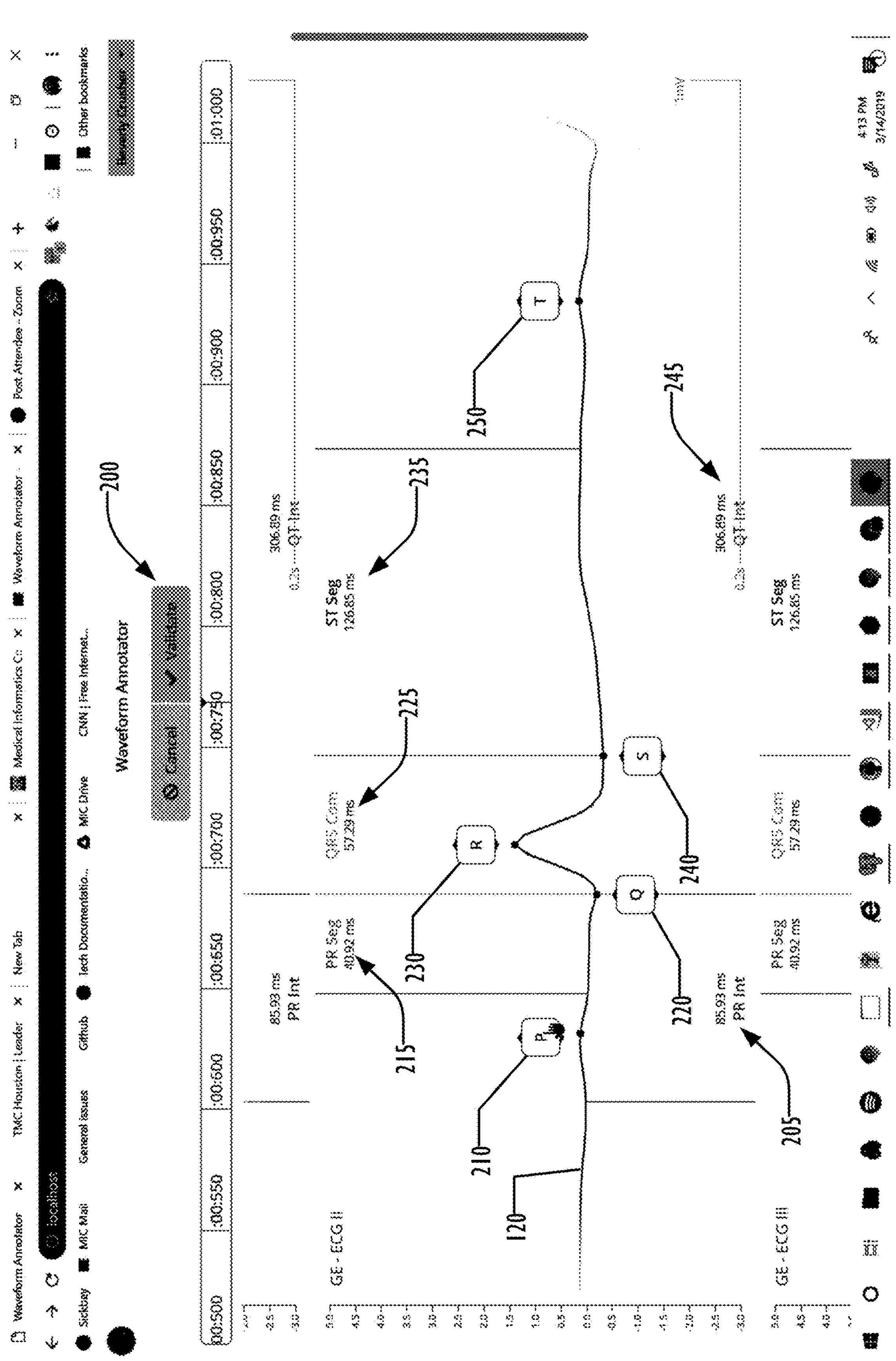
FIGS. 3-7 are screenshots illustrating user modifications to waveform annotations in the user interface of the waveform annotator according to one embodiment.

The annotation interface then allows the user to drag or otherwise modify the P, Q, R, S, and T markers 210, 220, 230, 240, and 250 across all leads, if the clinician using the interface believes those points were not correctly auto-detected and annotated. FIG. 3 is a screenshot illustrating that the user has dragged the R marker 230 slightly to the left of the waveform peak, instead of slightly to the right of the peak as in FIG. 2.

The modifications of the initial annotations illustrated in the figures and described herein is not intended to have any medical significance, but are merely illustrative of the capabilities of the waveform annotator system and examples of the kinds of annotation modifications that a user could make.

Figure 4:
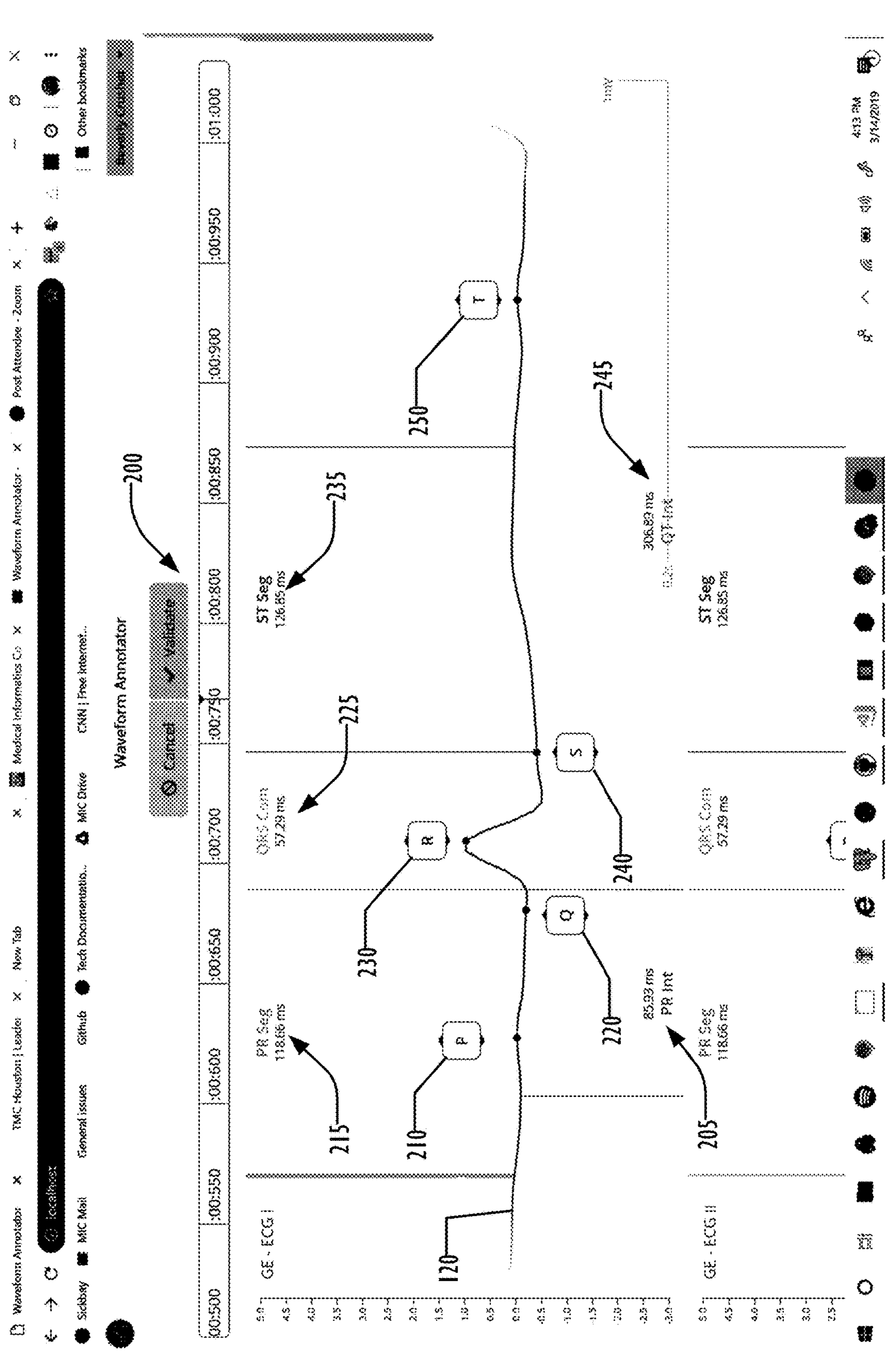
Figure 5:
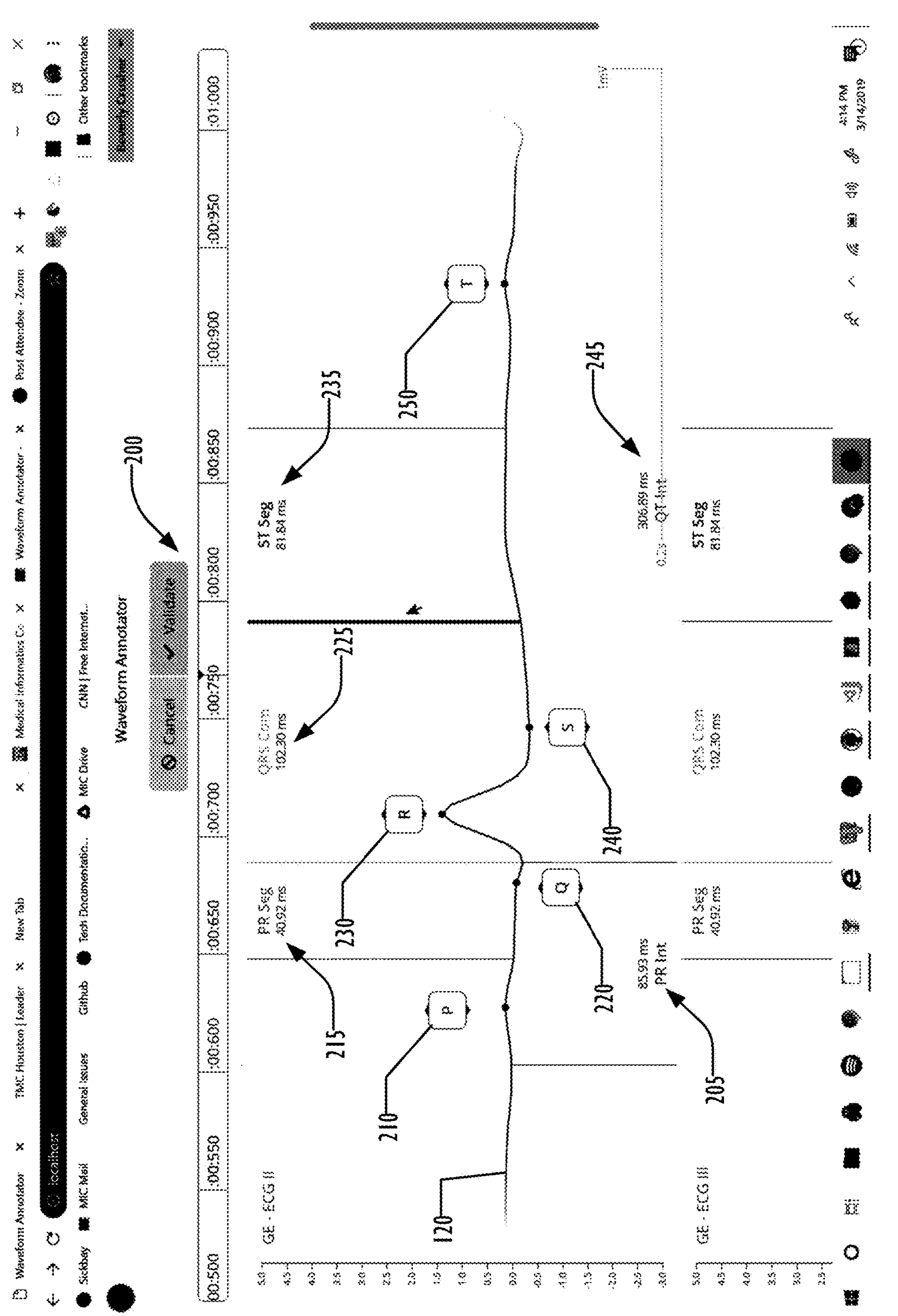

Similarly, as illustrated in FIG. 4, the user can use the interface to drag the beginning and endpoints of any of the segment features, causing the annotation interface to recalculate the millisecond interval between the beginning and endpoint of the segment may be displayed on the screen in the annotation interface. An adjacent segment is also automatically updated. In FIG. 4, the beginning point of the PR segment 215 has been dragged leftward (earlier) compared to the position in FIG. 3, increasing the size of the PR segment to 118.66 ms. Because in FIG. 4 moving the beginning point of the PR segment 215 does not affect the lengths of any of the other segments, they remain the same. However, in FIG. 5, the user has dragged the endpoint of the QRS complex rightward (later) compared to FIG. 3, which causes the ST segment beginning boundary to change, changing the length of the ST segment from 126.85 ms to 81.84 ms. In some embodiments, the annotation change to the segments may be independent of annotation changes to the P, Q, R, S, and T markers 210, 220, 230, 240, and 250, as illustrated in FIG. 5, where the ending boundary of the QRS complex 225 originally was aligned with the S marker 240 in FIG. 3, but are no longer aligned in FIG. 5.

Figure 19:
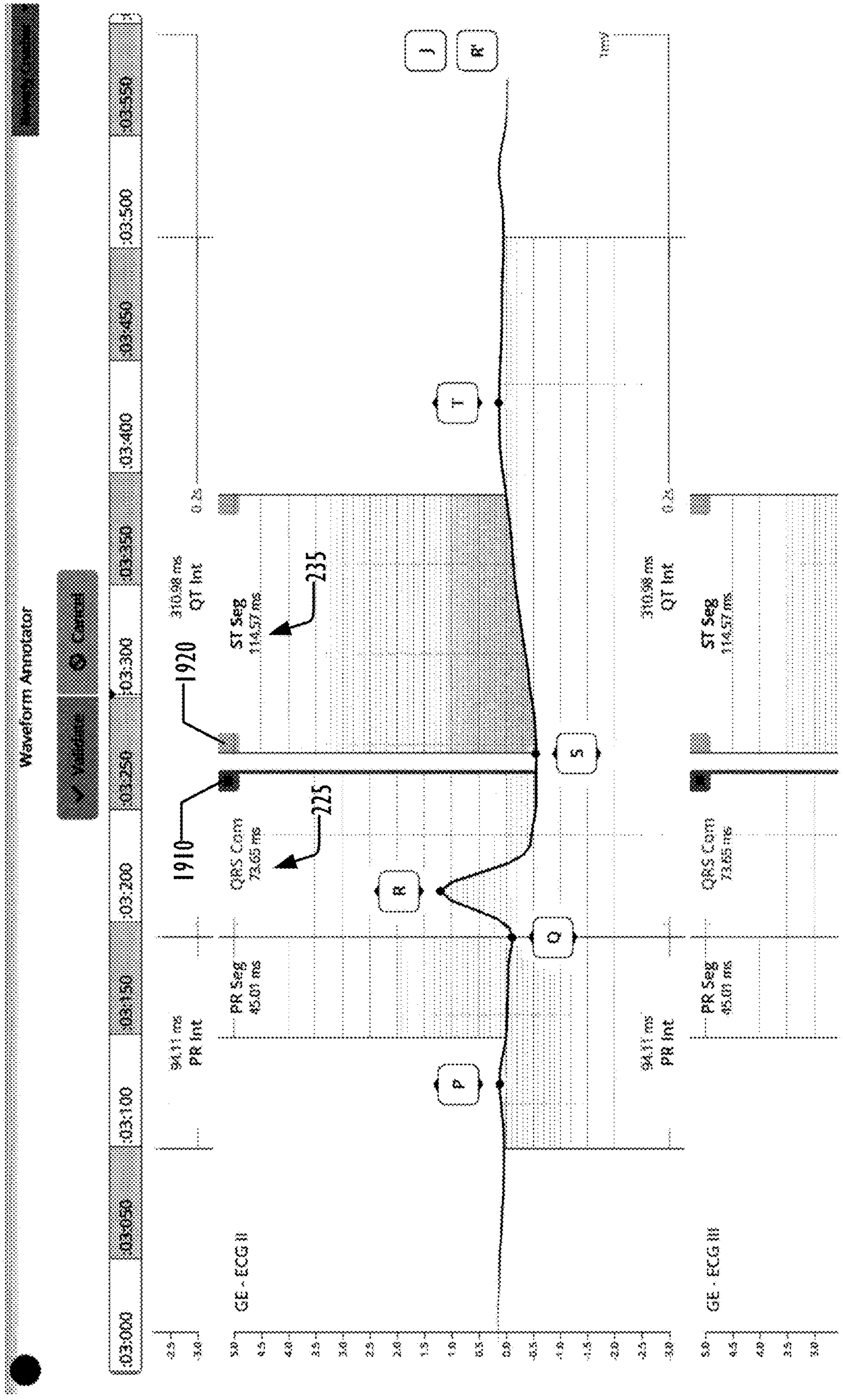
FIGS. 19-20 are screenshots illustrating de-linking and re-linking segment boundaries according to one embodiment.
Figure 20:
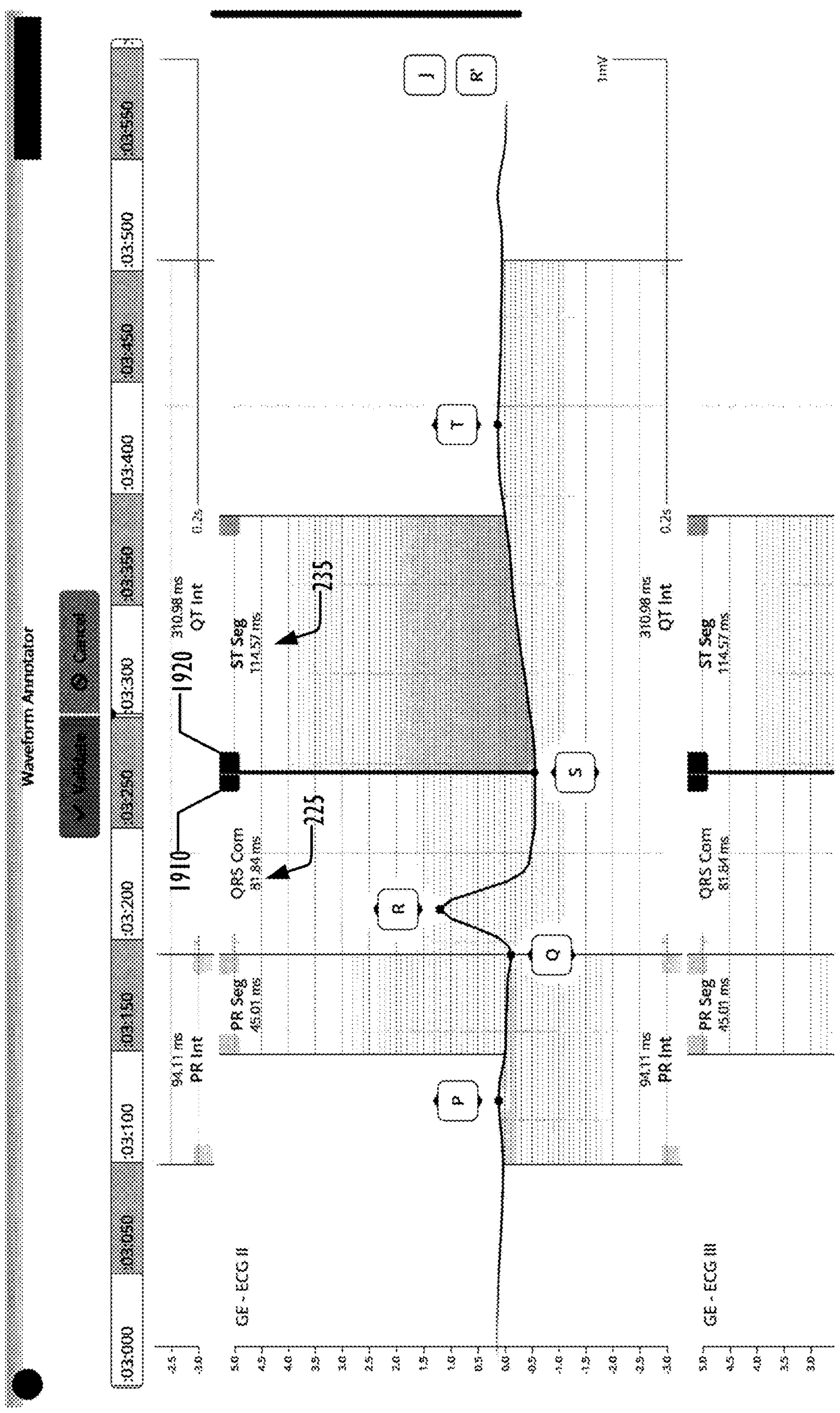

In one embodiment, the interface may allow de-linking adjacent segments. For example, as illustrated in FIGS. 19-20, the interface may allow the user to drag segment borders independently of one another using handles or other user interface elements associated with a segment boundary. In FIG. 19, handles 1910 and 1920 have been used to de-link the boundary of the QRS complex segment 225 from the boundary of the ST segment 235. In such an embodiment, the de-linked segment borders may be re-linked with the original adjacent segment or may be linked to another segment by dragging the segment border on top of another segment's border, as illustrated in FIG. 20. In one embodiment, an impending linkage may be indicated to the user by highlighting the borders of segments that are about to be linked.

Figure 6:
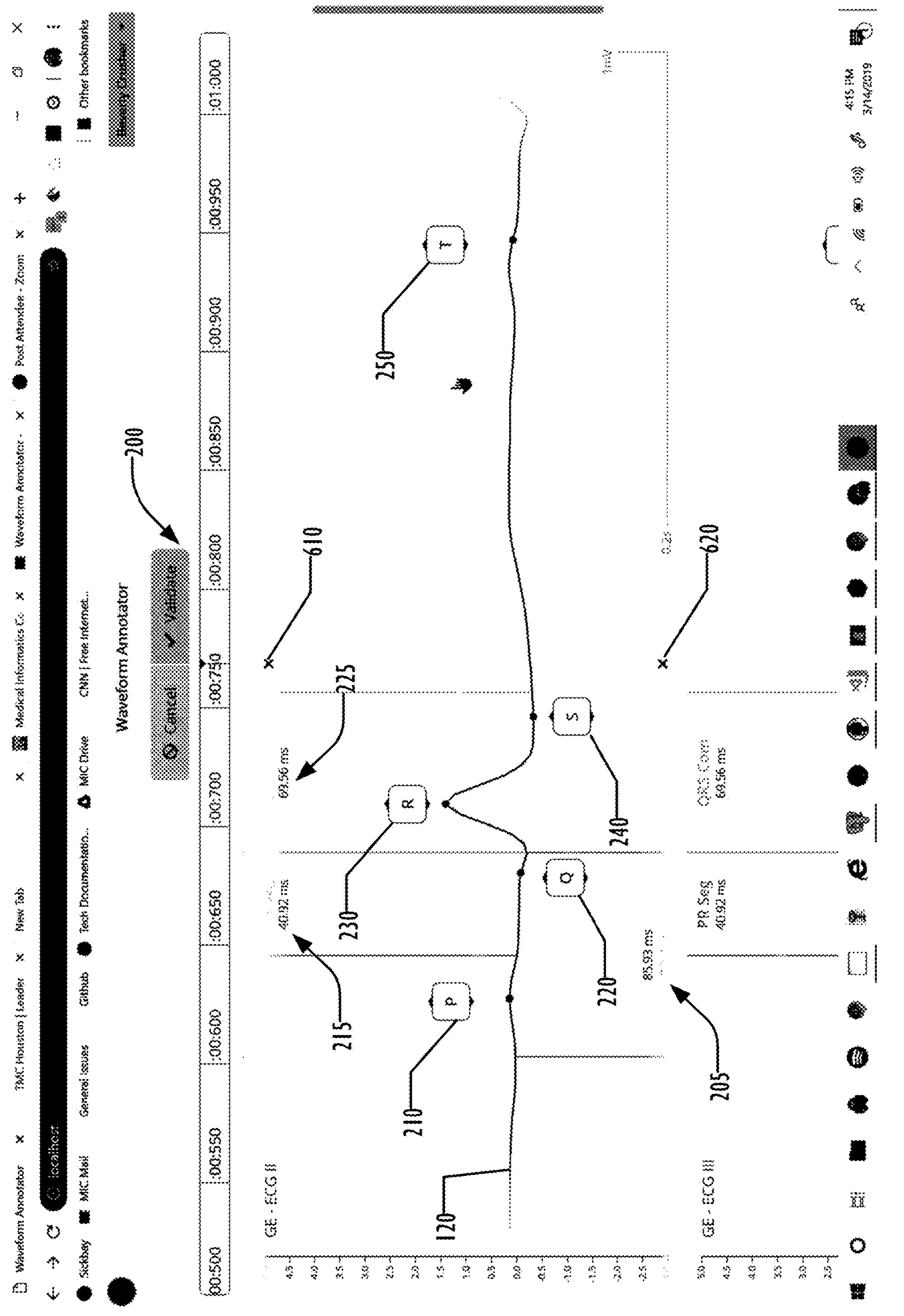
Figure 21:
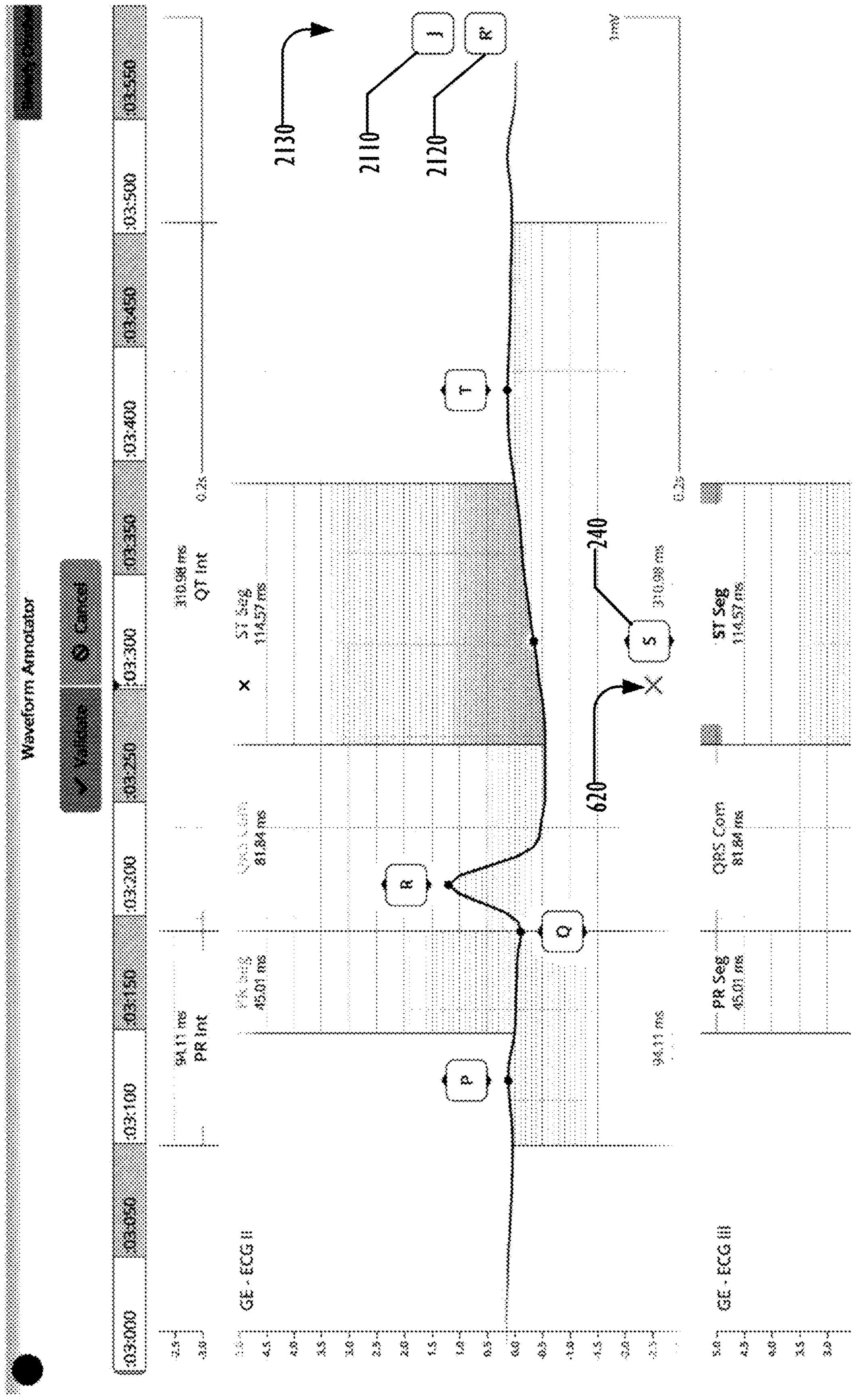
FIG. 21 is a screenshot illustrating a technique for removing a marker according to one embodiment.

As illustrated in FIG. 6, the waveform annotator system user interface 200 further allows the user to remove a segment from the annotation, should the user believe that reflects a heartbeat anomaly in the waveform 120. In FIG. 6, the ST segment 235 and QT interval 245 have been removed and are not shown in user interface. In some embodiments, an icon such as the icons 610, 620 may be displayed to indicate where an annotation such as T marker 250 may be dragged to remove it from the waveform, as illustrated in FIG. 21, where the S marker 240 is being removed by dragging to the icon 620. Although two icons 610 and 620 are illustrated in FIG. 6, the number and position of the icons 610, 620 are illustrative and by way of example only. Any desired number and position of an icon may be used. In some embodiments, icons such as 610, 620 may be omitted, and simply dragging the marker to a designated area, such as the tray area 2130, may be used to indicate the desire to remove a marker. In this example, a J marker 2110 and R' marker 2120 are displayed in the tray area 2130, indicating those annotations have been removed from the display. Other techniques for removing a marker from the display may be used.

In some embodiments, segments may be removed independently of one of the P, Q, R, S, and T markers 210, 220, 230, 240, 250. In other embodiments, the only way to remove a segment is to remove one or both of the associated annotations that define the segment. In some embodiments, if one of the markers P, Q, R, S, or T 210, 220, 230, 240, 250 are removed and corresponding segments are also removed, placing the removed P, Q, R, S, or T marker 210, 220, 230, 240, 250 back onto the waveform display will reestablish the corresponding segments, as well, assuming all other markers for that segment are present.

Figure 7:
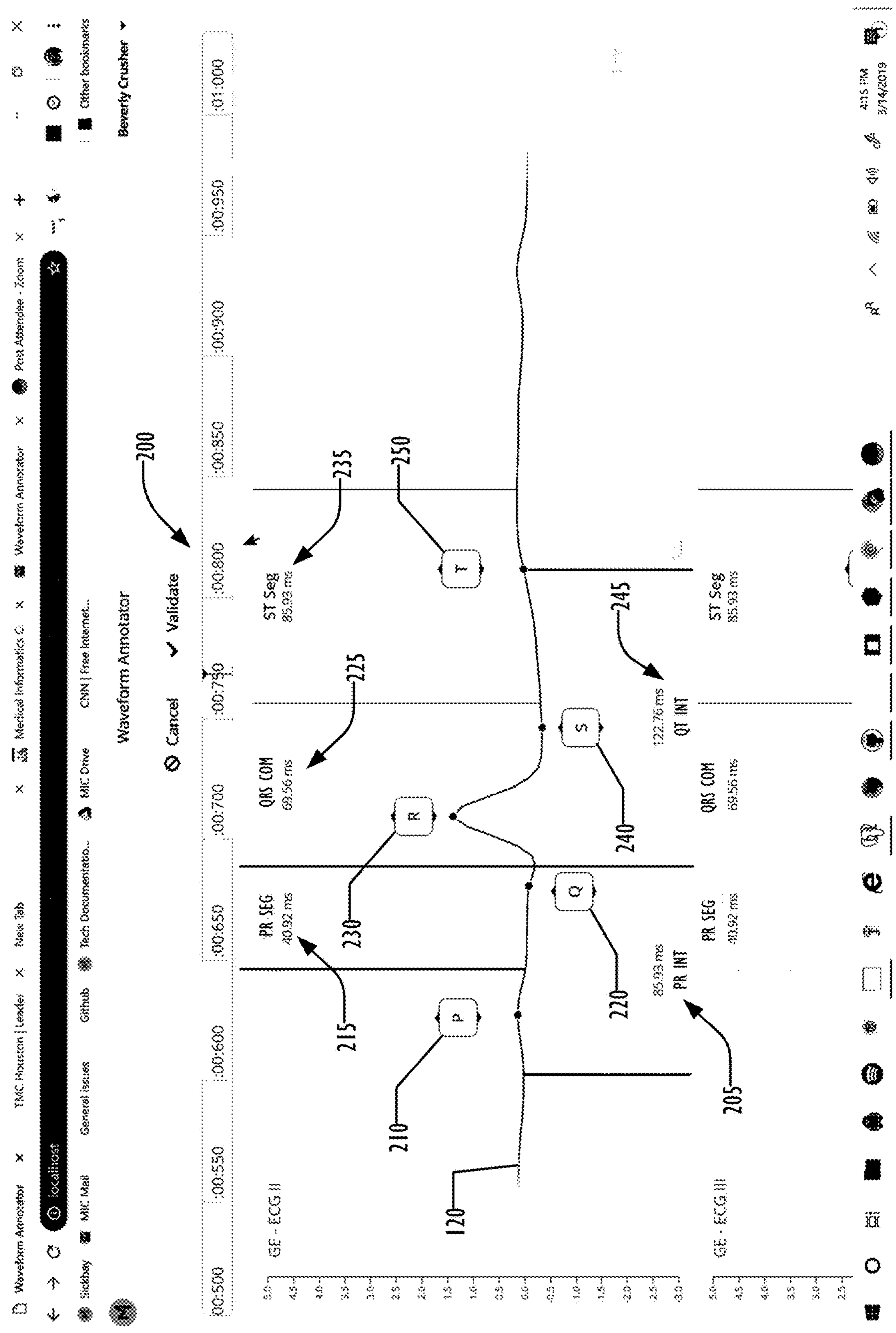

As illustrated in FIG. 7, in some embodiments, moving one of the P, Q, R, S, and T markers 210, 220, 230, 240, or 250 may automatically cause recalculation of related segments. In FIG. 7, the T marker 250 has been moved to the left compared to the annotation of FIG. 3, causing the QT interval endpoint boundary to be shifted leftward, resulting in a QT interval of 122.76 ms, instead of 306.89 ms as in FIG. 3. In other embodiments, markers and segments may be moved independently of each other, such that moving (for example) the T marker 250 has no effect on the boundaries of the QT interval endpoint boundary.

Figure 8:
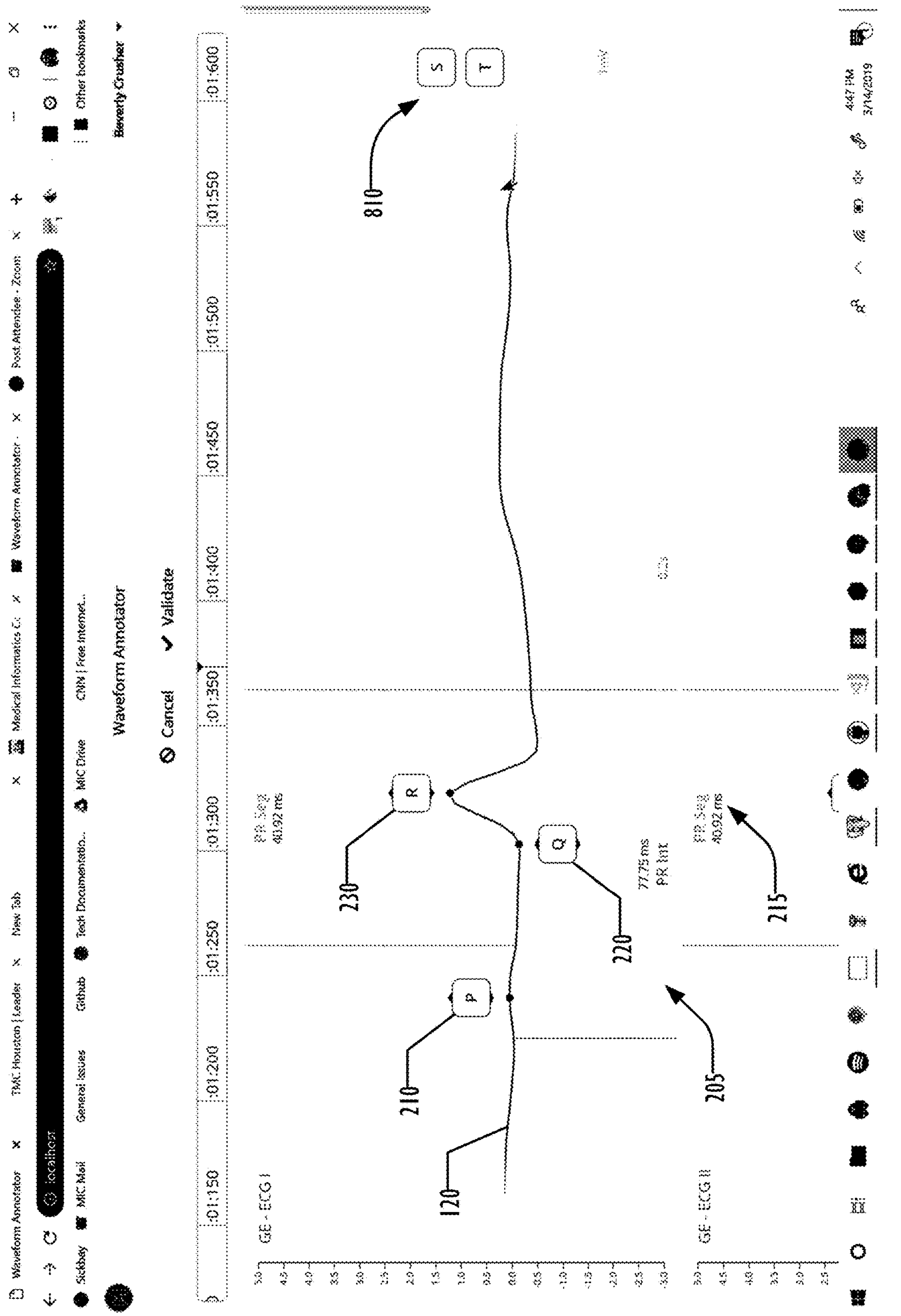
FIG. 8 is a screenshot illustrating removing annotations from a physiological data waveform in a user interface of the waveform annotator according to one embodiment.
Figure 14:
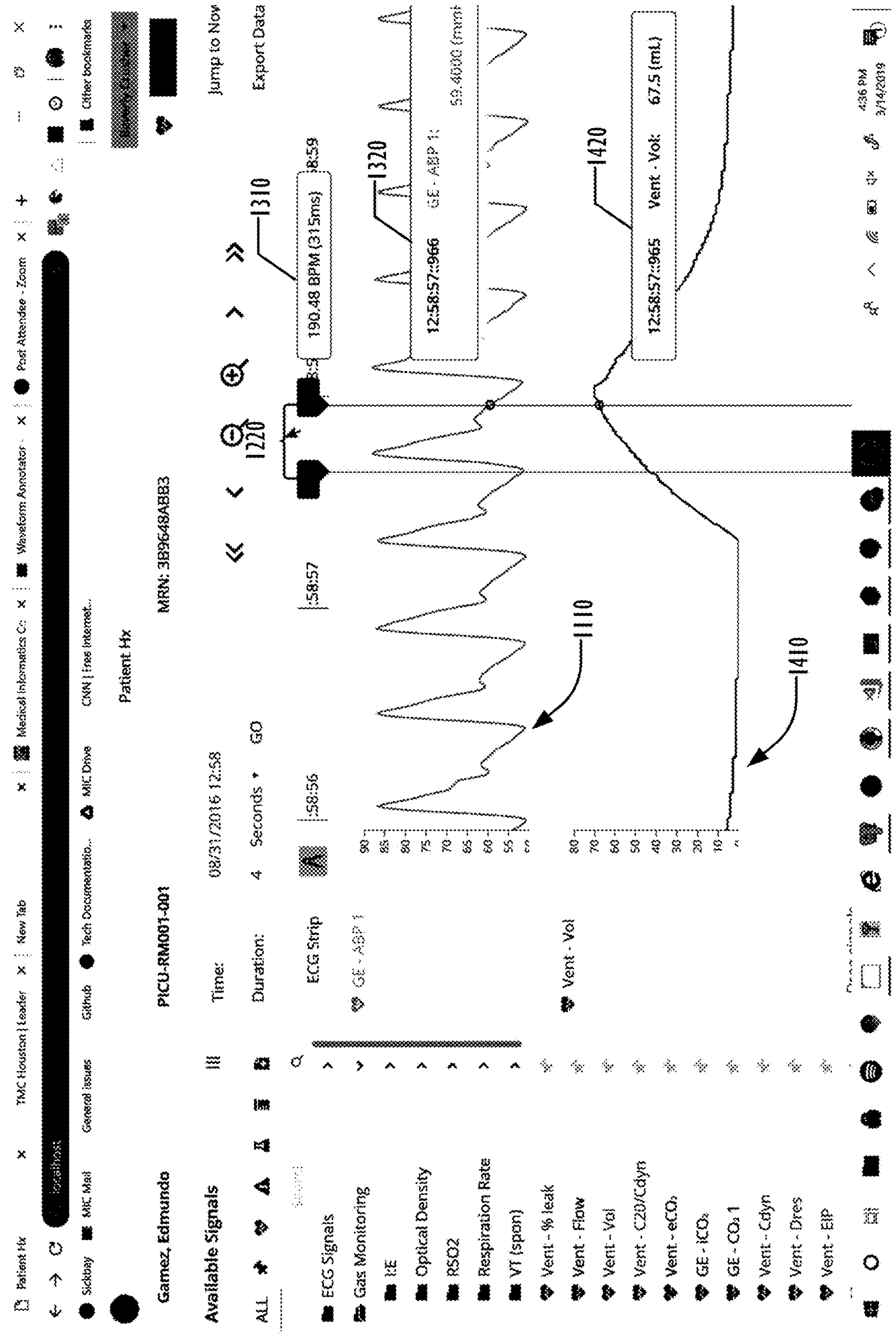

As illustrated in FIG. 8, the user can remove markers. In FIG. 14, the S and T markers 240, 250 have been removed and placed into a tray area 810. Any segment associated with the removed markers are also removed. Thus, in FIG. 8, the QRS complex, QT interval, and ST segment annotations have been removed from the display. Similarly, a marker such as a T marker 250, can be dragged from the tray area

810 onto the waveform 120 and associated segments may be identified and created in the interface as a result.

Once the clinician using the waveform annotator system is satisfied with the annotations, the clinician may approve the annotations by indicating that the annotations have been validated. In FIG. 2, this is illustrated by a Validate button 260.

Figure 9:
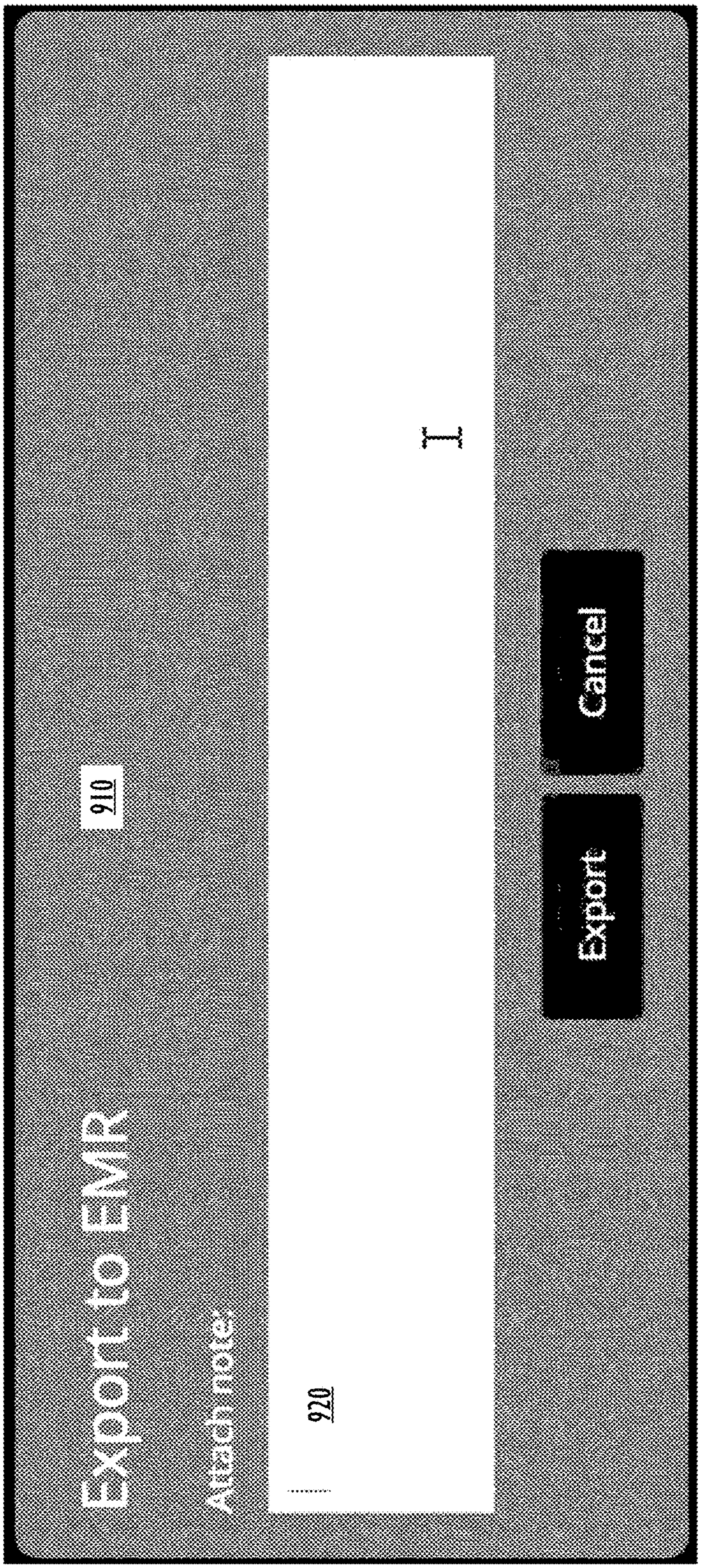
FIG. 9 is a screenshot illustrating a user interface of the waveform annotator according to one embodiment allowing saving an annotated waveform to an EMR system.

Once the annotations are approved by the clinician using the waveform annotator system, the annotations can be exported, such as to an EMR system, with additional user comments or notes on the annotation. Pop-up windows or other forms of user interface elements can be used for entering the user comments or notes. One example of such a user interface element is the window 910 of FIG. 9, which allows attaching notes to the data exported to the EMR system in area 920. In one embodiment, a text form of the annotations illustrated in FIGS. 2-8 can be included with additional user comments in the annotations exported to the EMR system, such as a note that the waveform exhibits an arrhythmia.

Figure 10:
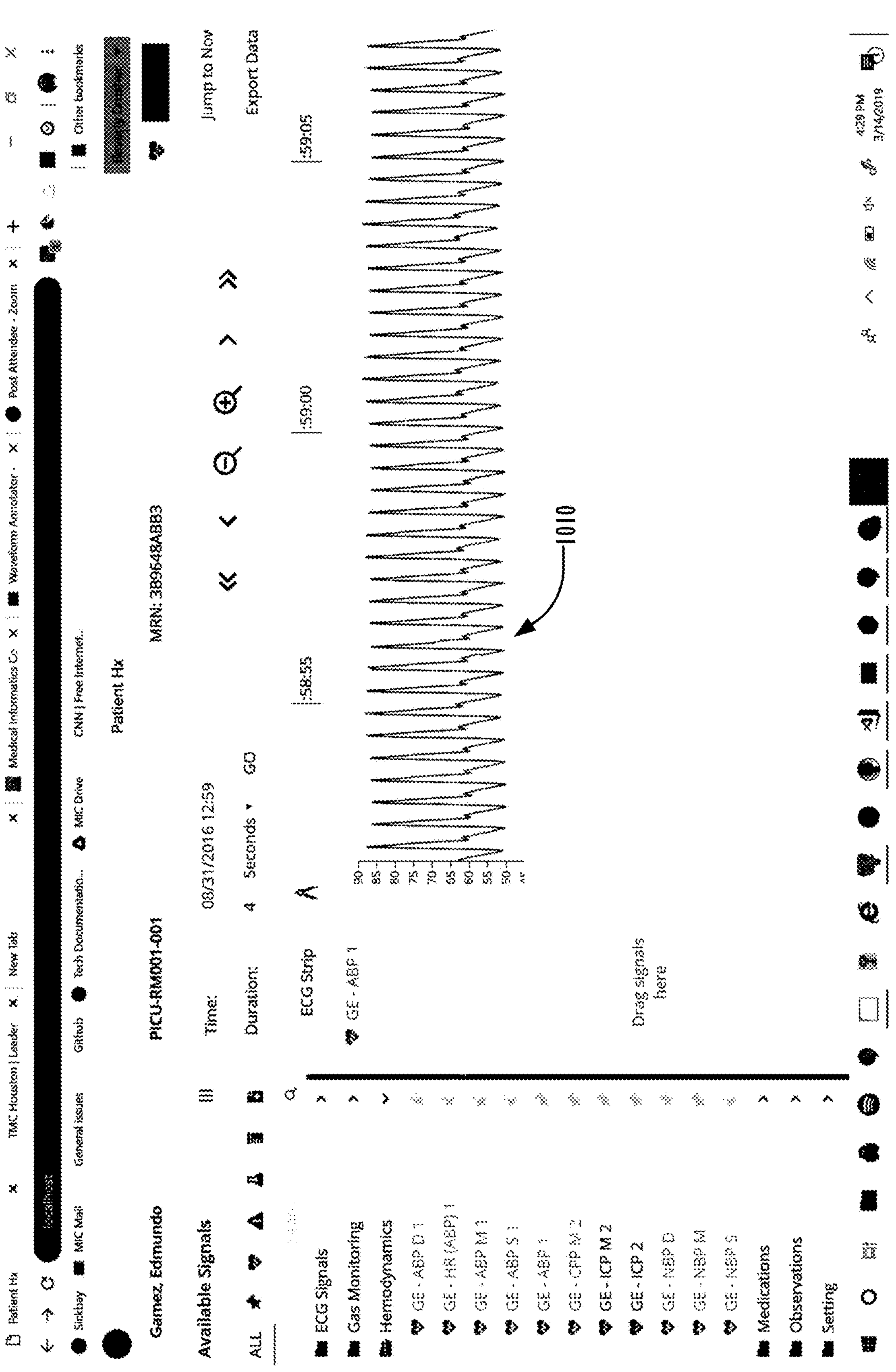
FIGS. 10-14 are screenshots illustrating annotating a second type of physiological data waveform in a user interface of the waveform annotator according to one embodiment.
Figure 11:
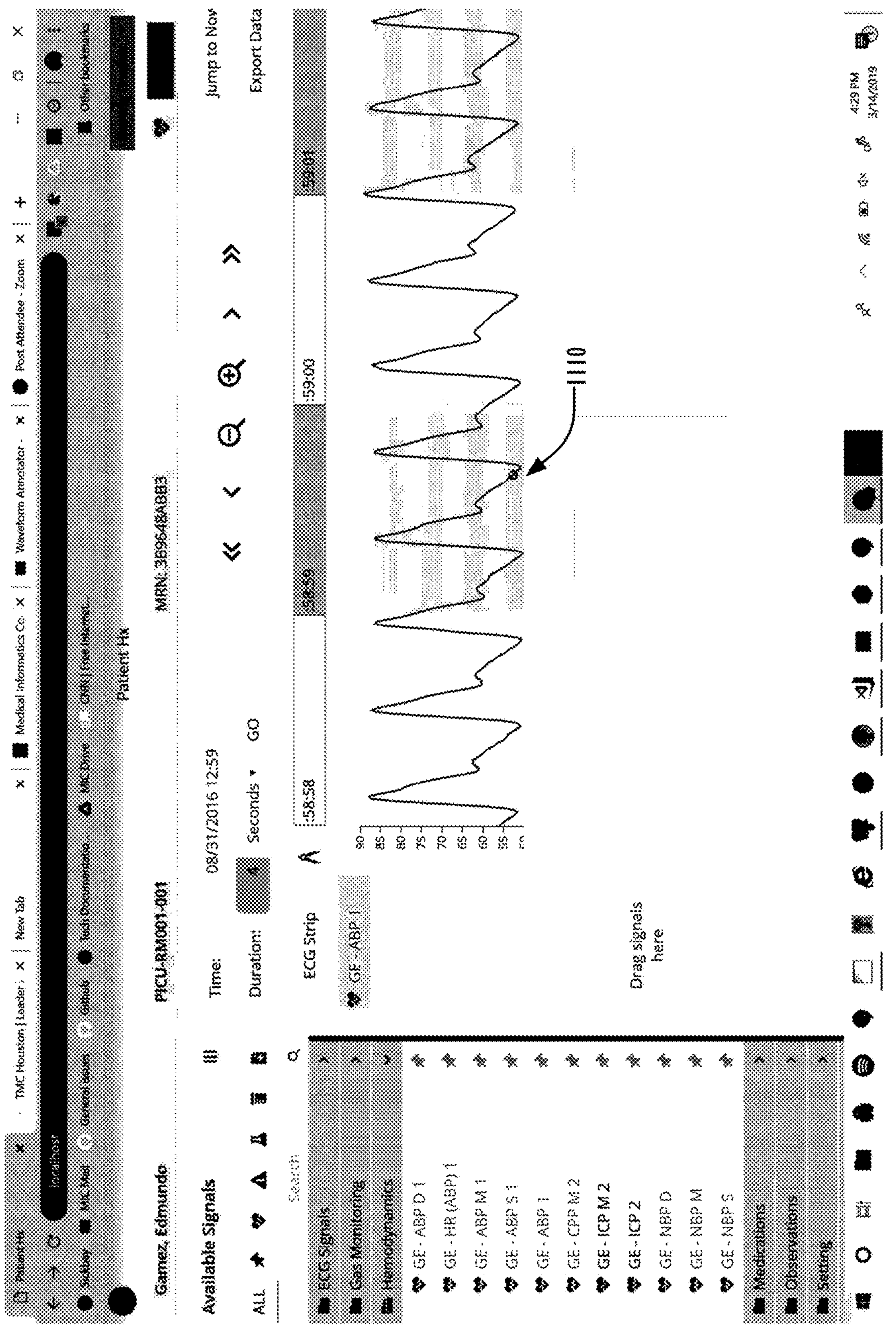

The same approach is used on other physiological waveforms, detecting time periods of interest. For example, FIG. 10 is a screenshot illustrating a waveform 1010 associated with arterial blood pressure (ABP) physiological data, an expanded form of which is shown as waveform 1110 in FIG. 11. If the initial model provides auto-detection of features in the ABP waveform, then those features may be placed automatically on the waveform 1110, similarly to the initial annotations illustrated in the ECG waveform display of FIG. 2.

The system can use machine learning to improve the detection of features and time periods of interest. As users add validated feature points into the system, the machine learning algorithm is retrained to recognize these new data labels. So, for example, if users determine that the R peak should be placed earlier than the initial algorithmic placement, over time the automatic location of the R peak will be adjusted accordingly.

Figure 12:
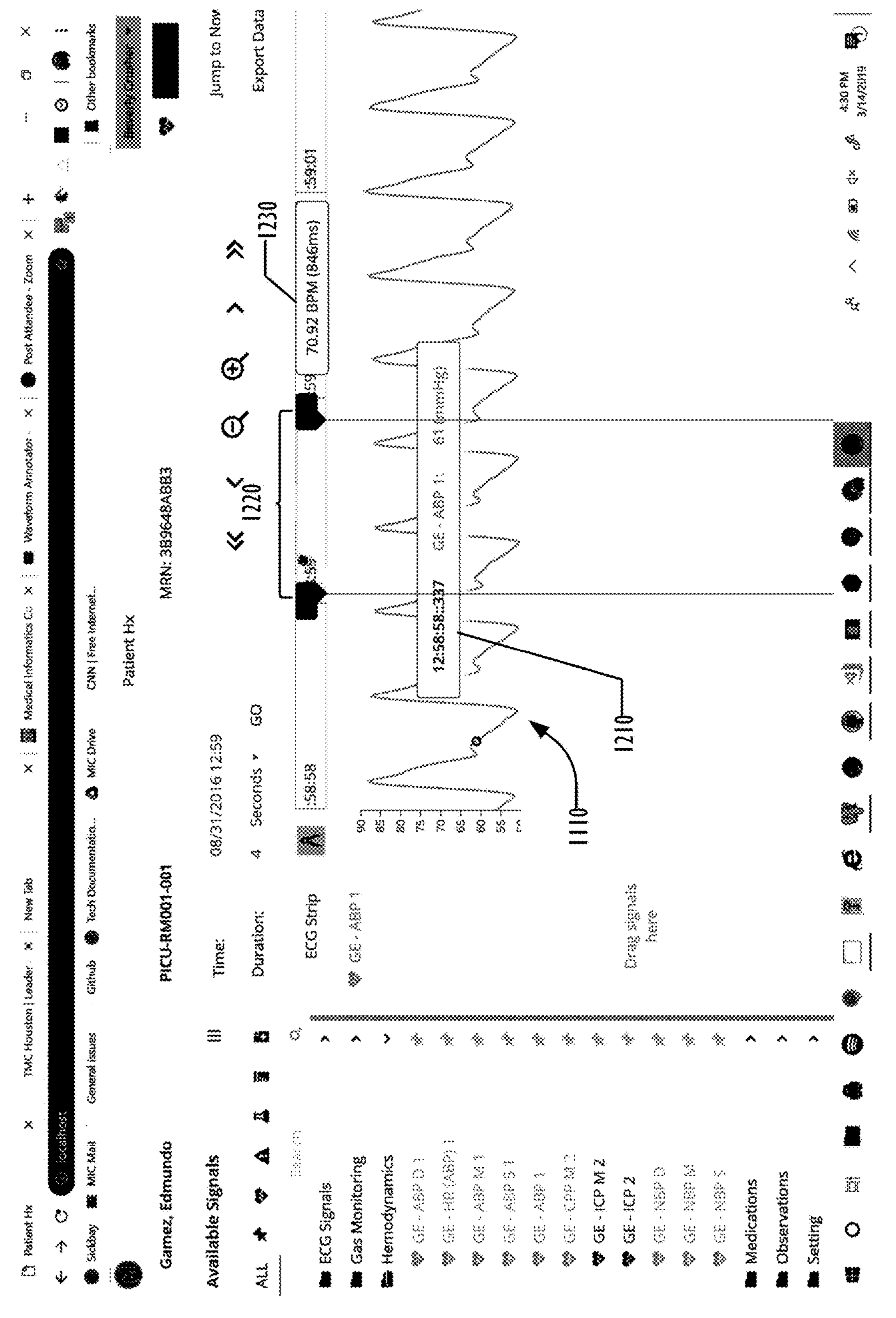
Figure 13:
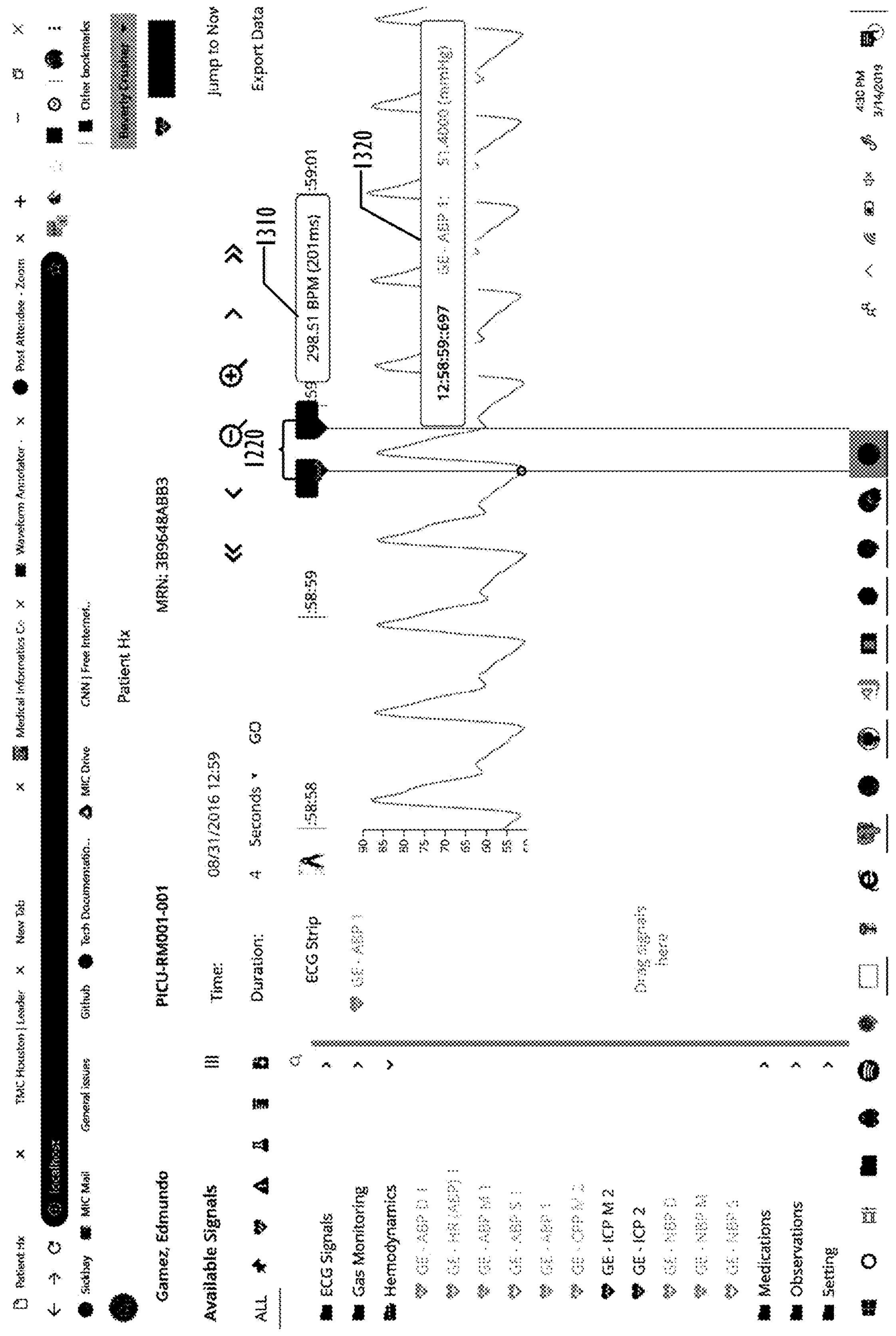

As illustrated in FIG. 12, in some embodiments, calipers 1220 may be used to mark a desired area on the waveform, causing the waveform annotator to generate automatic annotations of waveform, such the annotation 1210 indicating the ABP during that time period and annotation 1230 indicating the number of beats per minute. As illustrated in FIG. 13, the calipers 1220 may be moved, causing the resulting annotations 1310 and 1320 to be calculated accordingly. Although not illustrated in FIGS. 12-13, the waveform annotation system may be configured to calculate an area under the curve of the waveform, where that area under the curve has a medical significance. These automatic calculations could not be performed by a human being manually with the level of accuracy and precision that is possible with the waveform annotation system.

As illustrated in FIG. 14, annotations made to one type of waveform may be used with other types of waveforms to obtain more information, whether they are automatically placed or are modified or added by the clinician using the waveform annotator system. In the example of FIG. 14, the annotations 1310 and 1320 derived from the calipers 1220 may be generated for an ABP waveform 1110 as well as a ventilation volume waveform 1410, generating an annotation 1420 indicating the ventilation volume during the same time period as the ABP time period.

The waveform annotation system therefore provides a way of automatically generating annotations more quickly and with more accuracy and precision than could be accomplished manually. This model-based auto-detection of features and annotation generation is qualitatively different than the way in which clinicians make annotations manually, and may result in annotations that clinicians would not or could not have made, either because of time constraints or because the model used to generate the automatic initial annotations detected something that was not recognized by looking at the waveform.

Figure 15:
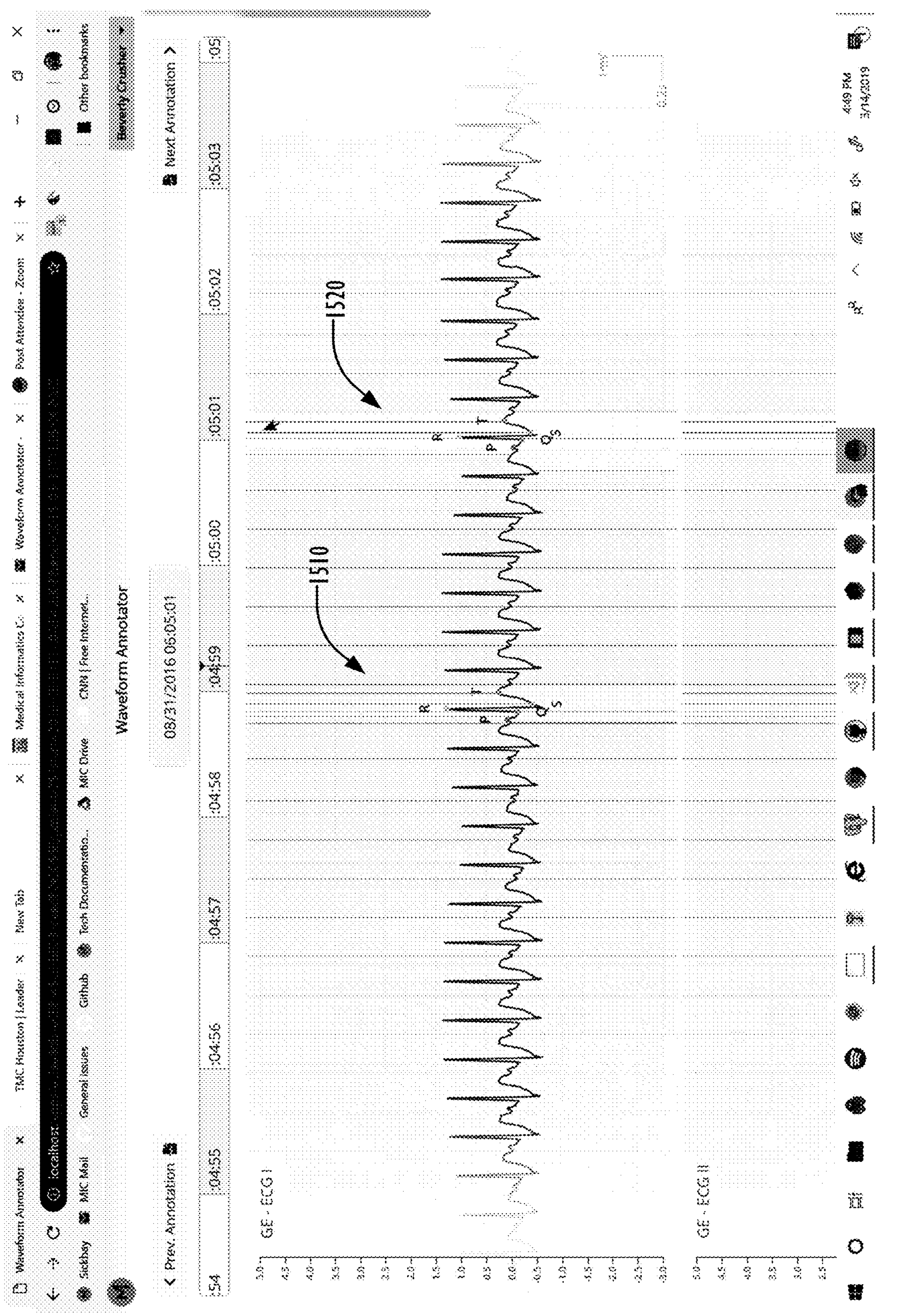
FIG. 15 is a screenshot illustrating annotation of multiple events in a physiological data waveform in a user interface of the waveform annotator according to one embodiment.

As illustrated in FIG. 15, which shows automatically generated annotation sets displayed in two different heartbeats at 1510 and 1520, the waveform annotation system can annotate more than a single heartbeat, but may make the annotations on multiple heartbeats (or instances of other repeating features that exist in non-ECG waveforms).

Embodiments of the system may provide annotations that are not commonly done today by clinicians. For example, an arterial blood pressure (ABP) waveform may be annotated to indicate features such as a dicrotic notch that are not commonly manually annotated in ABP waveforms, but which are known to have clinical significance.

In addition, embodiments of the waveform annotation system can provide annotations that are not possible in a manual annotation. For example, an annotation of the area under a curve can be generated automatically. Any other desired signal-based information can be calculated and added as an annotation, allowing documentation of features not documented previously. Because the annotations can be made on multiple events, such as on every heartbeat, the waveform annotation system can show the clinical personnel variations in the waveform data that might not be noticed otherwise.

For example, measurement of the QT segment is common in clinical settings to calculate variability of the heart. Instead of requiring the clinician to place calipers or other markers to generate a QT measurement in milliseconds, then creating a note saying that the QT segment was the measured length in milliseconds and pushing that note to the EMR as a scanned file, the waveform annotator system according to one embodiment may allow multiple annotations in the same interface to be created automatically and much faster. Similar to the way autofill allows a user to enter text faster with the autofill system suggesting text based on what is being entered, embodiments of the disclosed system may automatically suggest multiple annotations based on the known type of physiological waveform data, and do so in a way that those annotations can be modified, saved, and exported to an EMR system as desired.

In some embodiments, the annotations are stored in the local system platform, but de-identified physiological feature data can be used to train a machine learning algorithm. In one embodiment the training may be performed in the local system platform then the trained model may be distributed across other systems having this feature. Alternately, data from the local system platform may be sent to a central site for training the machine learning algorithm, and the updated models distributed. Distributed model fitting may be used to update the models used in other systems having the waveform annotation capability, while restricting the actual waveforms and related data to the local system for patient privacy reasons. Any desired technique for performing machine learning may be used to train the models used by the waveform annotator.

Continuous improvement in the automatically suggested annotations is provided using machine learning to adjust the model that detects and annotates features of the waveform. For example, if the initial model suggests an R peak at one position in the heartbeat, but clinicians constantly moves that initial R peak to the left (earlier), over time the model may be trained to reflect that in the automatically created annotation for the R peak.

Any desirable machine learning technique may be used to improve the automatic annotation based on the expert labeling made in the annotation.

In some embodiments, features of a healthy patient may not be present in the physiological waveform data, or features not normally present may be detected in the physiological waveform data. For example, in an ECG waveform, the S segment may be missing or a pacemaker sub-beat signal may be present. The waveform annotation system may automatically adjust the annotations to note the absence of a feature or the presence of a feature that is not normally present. In one embodiment, a user interface feature may show features that can be manually added if they are not automatically detected. Because of the continuous improvement provided by machine learning, a feature that is not detected automatically by the initial model may become automatically detectable after a sufficient number of expert labeling events that add manual annotations.

In one embodiment, a clinician can move in the waveform annotation user interface between annotations, by selecting an element to move to the next or previous annotation already made. The clinician may validate each annotation as desired, approving the validity of the annotation, before the annotations are stored in a database of annotations maintained by the waveform annotation system. Features may be removed from or modified in an annotation.

Because the annotations are stored in an annotation database, a clinician can switch from a first patient to a second patient, review and validate annotations for the second patient, then return to continue working with annotations previously made for the first patient, without having to make those annotations again. Where the underlying system allows modifying the scaling of the data, the annotations may be adjusted accordingly.

Figure 16:
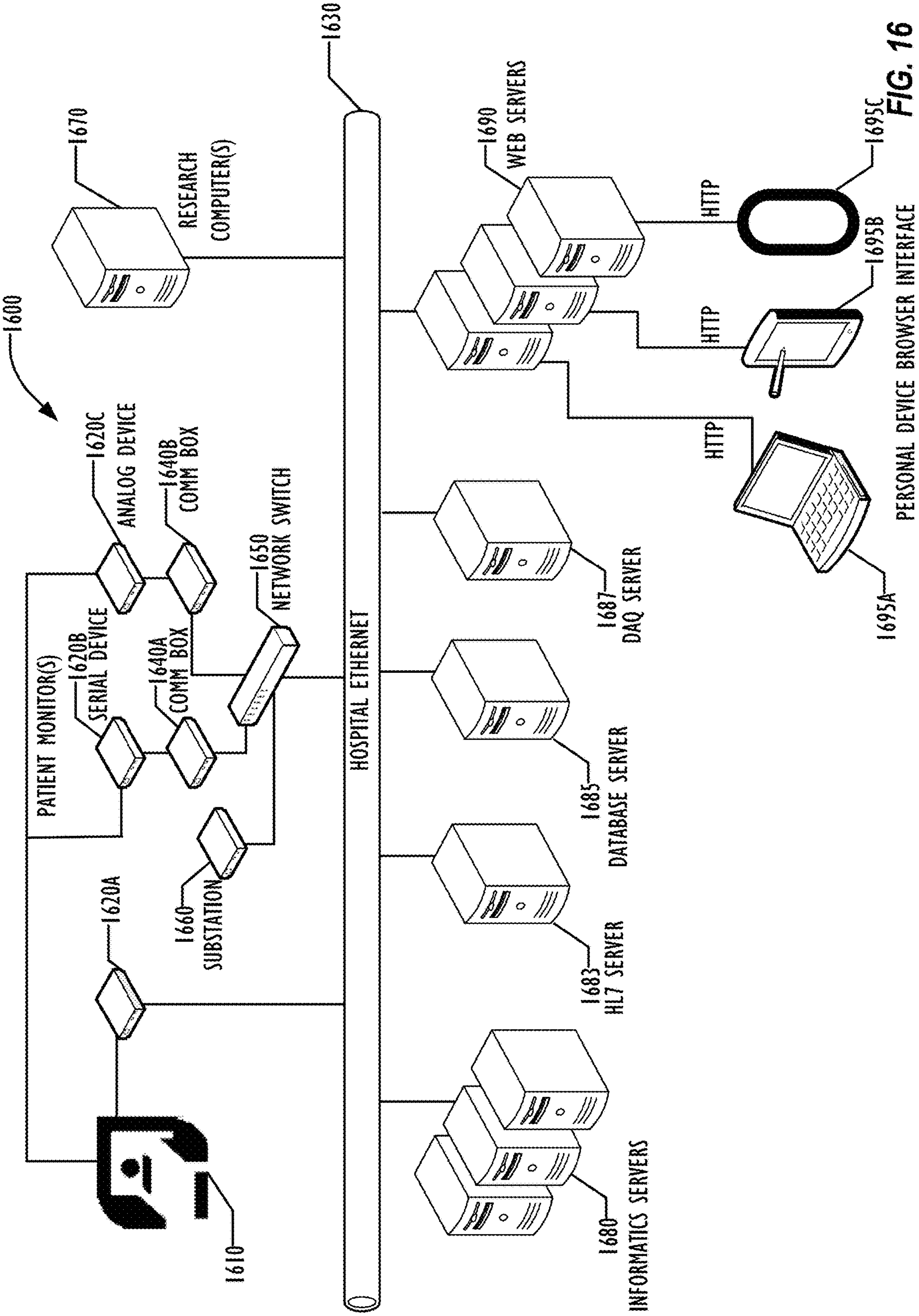
FIG. 16 is a block diagram of a system for collecting, analyzing, analyzing, and annotating physiological data according to one embodiment.

FIG. 16 is a block diagram illustrating a platform system 1600 for collecting, archiving, and processing arbitrary data in a healthcare environment according to one embodiment. The system 1600 may provide a waveform annotation system as part of the platform provided by the system 1600.

As illustrated, there are five types of servers: the data acquisition (DAQ) server 1687, the informatics server(s) 1680, the database server 1685, the HL7 server 1683, and the web server(s) 1690. Any number of any of the types of servers may be deployed as desired. All of the servers 1680-1690 connect to each other and the bedside monitors via one or more hospital networks 1630. Although illustrated as a single hospital Ethernet network 1630, any number of interconnected networks may be used, using any desired networking protocols and techniques.

Also connected to the hospital network 1630 are a number of bedside monitors for monitoring physiological data for a patient in bed 1610. These bedside monitors may include network connected monitors 1620A, which can deliver digital physiological data to the hospital network 1630, serial devices 1620B, which produce digital data but are not directly connected to a network, and analog devices 1620C, which produce analog data and are not directly connected to a network. Communication boxes 1640A and 1640B allow connecting the serial devices 1620B and analog devices 1620C, respectively, to the hospital network 1630, typically through a network switch 1650. In addition, a substation 1660 may be also connected to the network 1630 via the network switch 1650 for performing data manipulation and time synchronization as described below. Any number of bedside monitor devices 1620 may be used as determined advisable by physicians and other clinical staff for the patient in bed 1610.

Although as illustrated in FIG. 1 the bedside monitors and associated communication devices are connected directly or indirectly to the hospital network 1630, remote bedside monitoring devices may be used as part of the system 1600, such as home monitoring devices, connected to the hospital network 1630 indirectly through the Internet or through other communication techniques.

Additionally, one or more research computers 1670 may be connected, directly or indirectly, to the hospital network 1630, allowing researchers to access aggregated data collected from bedside monitors devices 1620 for performing analytics and development.

The web servers 1690 are configured for communicating with personal devices such as laptop 1695A, tablet 1695B, or smart phone 1695C via a web browser interface using HyperText Transport Protocol (HTTP). In the case of the waveform annotator system, in most embodiments the models and signal processing computation for performing the annotations are performed on one or more of the servers, such as the informatics servers 1680, and sent for display via the web servers 1690 for displaying the user interface on the personal devices 1695. However, in some embodiments, more computation may be performed on the personal devices 1695 as desired, dependent on the capabilities of the personal devices 1695.

Figure 17:
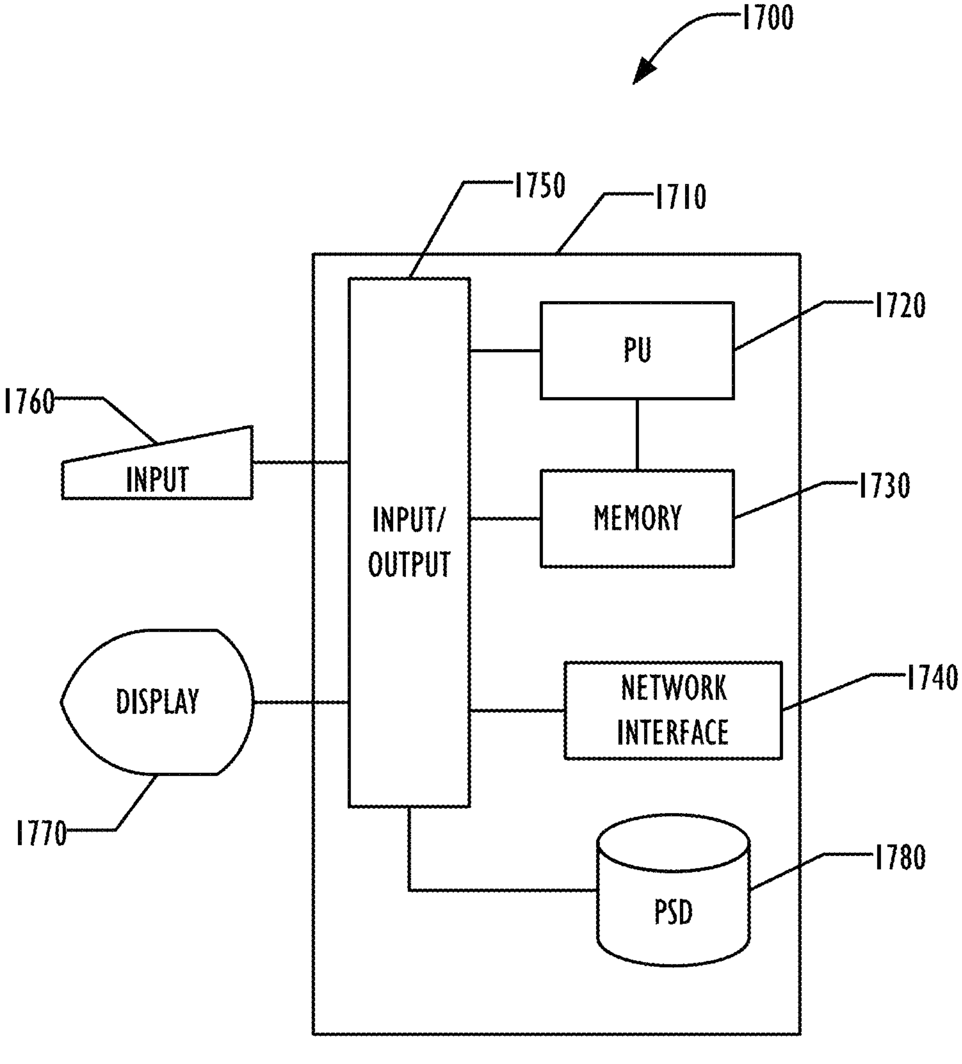
FIG. 17 is a block diagram of a computer for use in the system of FIG. 16 according to one embodiment.

Referring now to FIG. 17, an example computer 1700 for use as one of the servers 1680-1690 is illustrated in block diagram form. Example computer 1700 comprises a system unit 1710 which may be optionally connected to an input device or system 1760 (e.g., keyboard, mouse, touch screen, etc.) and display 1770. A program storage device (PSD) 1780 (sometimes referred to as a hard disc) is included with the system unit 1710. Also included with system unit 1710 is a network interface 1740 for communication via a network with other computing and corporate infrastructure devices (not shown). Network interface 1740 may be included within system unit 1710 or be external to system unit 1710. In either case, system unit 1710 will be communicatively coupled to network interface 1740. Program storage device 1780 represents any form of non-volatile storage including, but not limited to, all forms of optical and magnetic, including solid-state, storage elements, including removable media, and may be included within system unit 1710 or be external to system unit 1710. Program storage device 1780 provides a machine readable medium that may be used for (a) storage of software in the form of instructions that when executed cause the control system unit 1710 to perform desired actions, (b) data for use by the computer 1700, or both.

System unit 1710 may be programmed to perform methods in accordance with this disclosure (an example of which is in FIG. 4). System unit 1710 comprises a processor unit (PU) 1720, input-output (I/O) interface 1750 and memory 1730. Processing unit 1720 may include any programmable controller device, such as microprocessors available from Intel Corp. and other manufacturers. Memory 1730 may include one or more memory modules and comprise random access memory (RAM), read only memory (ROM), programmable read only memory (PROM), programmable read-write memory, and solid-state memory. One of ordinary skill in the art will also recognize that PU 1720 may also include some internal memory including, for example, cache memory.

Figure 18:
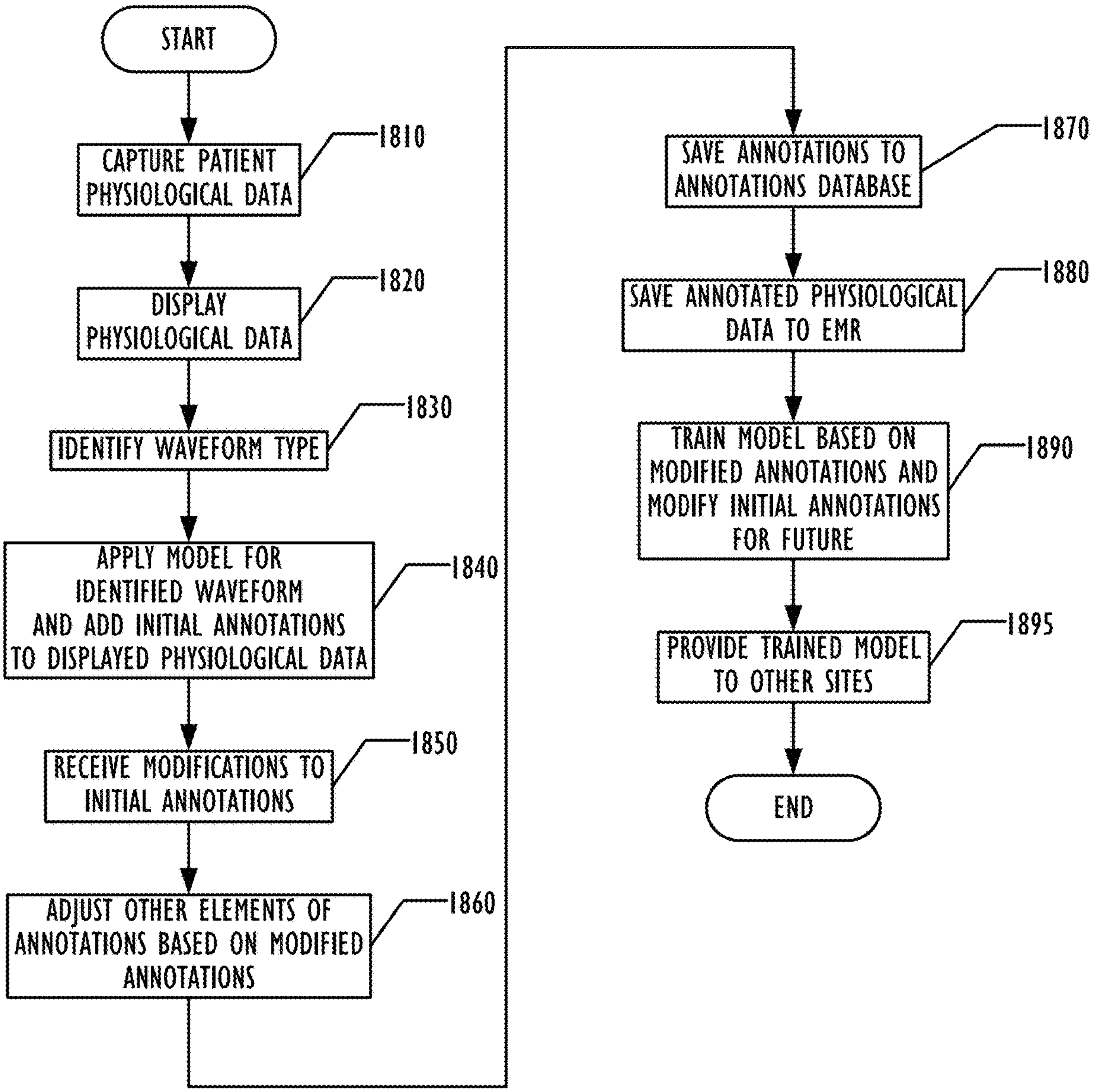
FIG. 18 is a flowchart illustrating a technique for annotating physiological data waveforms by a waveform annotator according to one embodiment.

FIG. 18 is a flowchart illustrating the techniques described above for annotating physiological waveform data according to one embodiment. The order and grouping of actions illustrated in FIG. 18 is illustrative and by way of example only, and the actions may be performed in other orders, or may be combined differently than illustrated in FIG. 18. In block 1810, physiological data from a patient is captured by the underlying platform system, such as the system illustrated in FIG. 16. Appropriate waveforms are generated and displayed in block 1820 when selected by the clinician. In block 1830, the waveform type displayed may be identified, either by signal analysis of the waveform or by using predefined waveform type information that is provided with the waveform. In some embodiments, all physiological data available in the underlying platform 1600 carries information identifying the type of physiological data.

In block 1840, the current model and algorithms for the identified waveform are applied to the waveform data to add initial annotations to the displayed physiological waveform, as illustrated in FIGS. 1-15 and described above. If the clinician believes the initial annotations are sufficient, nothing more need to be done with the annotations at this time.

However, if the clinician believes that the initial annotations are incorrect or insufficient, the clinician may use the user interface of the waveform annotator system as described above to modify the initial annotations, such as changing the location of markers in the display. These modifications are received by the waveform annotator system in block 1850.

In block 1860, the modified annotations may cause other annotations or ancillary data presented in the display to be modified. For example, as in FIG. 5 and described above, changing an endpoint of a QRS complex 225 may also cause changing the beginning point of the corresponding ST segment 235.

In block 1870, the annotations, whether the initial annotations automatically created by the waveform annotator or the modified annotations made by the clinician, may be saved for later use in an annotation database managed by the database server 1685. This allows a clinician to return to a previously viewed waveform without having to recreate the annotations, something that would not be possible in conventional systems that depend mostly on manual annotations made on printed versions of the waveform and annotations. In block 1880, the clinician may direct the waveform and saved annotations to be saved to an EMR system, possibly with additional textual annotations.

Another advantage of saving the annotations in the annotation database is that in block 1890, the initial model used to generate the automatically generated initial annotations may use the annotations as modified by the clinician for machine learning, training the model over time to improve and modify the initial annotations for future clinical use, creating a trained model based on the changes made by the clinician as described above. In block 1895, the trained model may be distributed to remote sites using the waveform annotator system. Similarly, the model used by the waveform annotator system may itself be updated or replaced by trained models received from remote sites that performed similar machine learning training. In one embodiment, updating the model may update automatically generated annotations that were not validated by the user, but may not update user-modified annotations or automatically generated annotations that have been validated by the user.

In addition to better placement of annotations, the use of machine learning techniques based on saved annotations allows the waveform annotation system to include new annotations that become clinically useful to clinicians, potentially saving lives and the health of patients through the use of better annotations.

By providing clinicians an initial set of waveform-specific annotations based on a machine-learning enhanced model, then allowing the clinician to modify or enhance the waveform annotations, saving the annotations for later use by either the clinician or for machine learning enhancement of the model, the waveform annotator system provides a different approach to the traditional technique of manually annotating waveforms. The automatic generation of annotations is faster than the manual techniques, and helps reduce the possibility that a clinician might fail to make a clinically important annotation. Because the annotations undergo continual improvement based on machine learning, the system over time adapts to changes in clinical knowledge without the need to specific programming updates.

Therefore, the waveform annotator system provides a technical solution to problems related to annotation of physiological data waveforms that satisfies a long-felt need for a different way to annotate physiological data waveforms.

The above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

We claim:

1. A method of annotating physiological waveform data, comprising:

analyzing a physiological data waveform corresponding to a first type of physiological data, based on a model corresponding to the first type of physiological data;

generating a first annotation automatically corresponding to the physiological data waveform based on the model, wherein the first annotation corresponds to a repeating feature of the physiological data waveform;

sending the physiological data waveform to a user display device;

sending the first annotation to the user display device for display on the physiological data waveform with the corresponding repeating feature of the physiological data waveform;

receiving a modification to the first annotation, wherein the modification repositions the first annotation on the physiological data waveform;

creating a second annotation based on the modification;

saving the second annotation in an annotation database; and training the model using machine learning based on the second annotation and the physiological data waveform, generating a trained model.

2. The method of claim 1, further comprising:

analyzing the physiological data to determine the first type of physiological data.

3. The method of claim 1, further comprising:

applying the first annotation to a plurality of instances of the repeating feature.

4. The method of claim 1, further comprising:

distributing the trained model for use by others.

5. The method of claim 1, further comprising:

receiving a trained model from a remote site; and replacing the model with the trained model.

6. The method of claim 1, further comprising:

displaying the second annotation with the physiological data waveform; and updating other annotations based on the modification to the first annotation.

7. The method of claim 1, further comprising:

sending the physiological data waveform and the second annotation to an electronic medical records system.

8. A non-transitory machine-readable medium, on which are stored instructions for a machine, comprising instructions that when executed cause the machine to:

analyze a physiological data waveform corresponding to a first type of physiological data, based on a model corresponding to the first type of physiological data;

generate a first annotation automatically corresponding to the physiological data waveform based on the model, wherein the first annotation corresponds to a repeating feature of the physiological data waveform;

send the physiological data waveform to a user display device;

send the first annotation to the user display device for display on the physiological data waveform with the corresponding repeating feature of the physiological data waveform;

receive a modification to the first annotation, wherein the modification repositions the first annotation on the physiological data waveform;

create a second annotation based on the modification;

save the second annotation in an annotation database; and train the model using machine learning based on the second annotation and the physiological data waveform, generating a trained model.

9. The non-transitory machine-readable medium of claim 8, wherein the instructions further comprise instructions that when executed cause the machine to:

analyze the physiological data to determine the first type of physiological data.

10. The non-transitory machine-readable medium of claim 8, wherein the instructions further comprise instructions that when executed cause the machine to:

apply the first annotation to a plurality of instances of the repeating feature.

11. The non-transitory machine-readable medium of claim 8, wherein the instructions further comprise instructions that when executed cause the machine to:

distribute the trained model for use by others.

12. The non-transitory machine-readable medium of claim 8, wherein the instructions further comprise instructions that when executed cause the machine to:

receive a trained model from a remote site; and replace the model with the trained model.

13. The non-transitory machine-readable medium of claim 8, wherein the instructions further comprise instructions that when executed cause the machine to:

display the second annotation with the physiological data waveform; and update other annotations based on the modification to the first annotation.

14. The non-transitory machine-readable medium of claim 8, further comprising:

send the physiological data waveform and the second annotation to an electronic medical records system.

15. A waveform annotator system, comprising:

a database of physiological data;

a database of waveform annotation data; and a processor, programmed to:

analyze a physiological data waveform corresponding to a first type of physiological data, based on a model corresponding to the first type of physiological data;

generate a first annotation automatically corresponding to the physiological data waveform based on the model, wherein the first annotation corresponds to a repeating feature of the physiological data waveform;

send the physiological data waveform to a user display device;

send the first annotation to the user display device for display on the physiological data waveform with the corresponding repeating feature of the physiological data waveform;

receive a modification to the first annotation, wherein the modification repositions the first annotation on the physiological data waveform;

create a second annotation based on the modification;

save the second annotation in an annotation database; and train the model using machine learning based on the second annotation and the physiological data waveform, generating a trained model.

16. The waveform annotator system of claim 15, wherein the processor is further programmed to:

analyze the physiological data to determine the first type of physiological data.

17. The waveform annotator system of claim 15, wherein the processor is further programmed to:

apply the first annotation to a plurality of instances of the repeating feature.

18. The waveform annotator system of claim 15, wherein the processor is further programmed to:

distribute the trained model for use by others.

19. The waveform annotator system of claim 15, wherein the processor is further programmed to:

display the second annotation with the physiological data waveform; and update other annotations based on the modification to the first annotation.

20. The waveform annotator system of claim 15, wherein the processor is further programmed to:

send the physiological data waveform and the second annotation to an electronic medical records system.

* * * * *